United States Patent
Kubo et al.

[11] Patent Number: 6,147,749
[45] Date of Patent: Nov. 14, 2000

[54] METHOD AND APPARATUS FOR MEASURING CONCENTRATION BY LIGHT PROJECTION

[75] Inventors: Hiroko Kubo; Yoshio Mitsumura; Harumi Uenoyama; Kexin Xu, all of Kyoto, Japan

[73] Assignees: Kyoto Daiichi Kagaku Co., LTD, Kyoto; Kurashiki Boseki Kabushiki Kaisha, Okayama, both of Japan

[21] Appl. No.: 08/817,085

[22] PCT Filed: Aug. 7, 1996

[86] PCT No.: PCT/JP96/02223

§ 371 Date: Apr. 7, 1997

§ 102(e) Date: Apr. 7, 1997

[87] PCT Pub. No.: WO97/06423

PCT Pub. Date: Feb. 20, 1997

[30] Foreign Application Priority Data

Aug. 7, 1995 [JP] Japan .................................. 7-200950

[51] Int. Cl.[7] .......................... G01N 33/48; G01N 21/00; A61B 5/00

[52] U.S. Cl. .............................. 356/39; 356/436; 600/310

[58] Field of Search ...................... 356/39, 436; 600/310, 600/314; 378/205

[56] References Cited

U.S. PATENT DOCUMENTS

| | | | |
|---|---|---|---|
| 4,000,417 | 12/1976 | Adkisson et al. | 356/39 |
| 4,171,866 | 10/1979 | Tolles | 356/39 |
| 4,513,438 | 4/1985 | Graham et al. | 356/39 |
| 4,700,298 | 10/1987 | Palcic et al. | 356/39 |
| 5,436,455 | 7/1995 | Rosenthal et al. . | |
| 5,446,548 | 8/1995 | Gerig et al. | 356/375 |
| 5,460,177 | 10/1995 | Purdy et al. . | |
| 5,531,520 | 7/1996 | Grimson et al. | 382/131 |
| 5,601,079 | 2/1997 | Wong et al. | 128/633 |
| 5,610,399 | 3/1997 | Müller et al. . | |

FOREIGN PATENT DOCUMENTS

| | | |
|---|---|---|
| 0623306A1 | 11/1994 | European Pat. Off. . |
| 4341063A1 | 6/1994 | Germany . |
| 1184447 | 7/1989 | Japan . |
| 3167460 | 7/1991 | Japan . |
| 4109932 | 4/1992 | Japan . |
| 510806 | 3/1993 | Japan . |
| 5508336 | 11/1993 | Japan . |
| 06014906A | 1/1994 | Japan . |
| 6503728 | 4/1994 | Japan . |
| WO9200513 | 1/1992 | WIPO . |
| WO9203965 | 3/1992 | WIPO . |
| WO 95/05599 | 2/1995 | WIPO . |

*Primary Examiner*—Frank G. Font
*Assistant Examiner*—Zandra V. Smith

[57] ABSTRACT

To project measuring light with good reproducibility onto the measuring part of a measured object so that measurement conditions can always be constant. An optical measuring apparatus is equipped with a spectroscopic analyzer that detects the spectral intensity of the reflected light of measuring light projected onto a human hand. Spectroscopic analyzer moves in the direction" of the X-axis, Y axis, and Z axis, and around the Z axis by a moving mechanism. During the registration of the measuring part of the human hand, a CCD camera takes a picture of the human hand, and the operator selects a part having a feature from the pattern of the taken image. During the spectrometry, the CCD camera again takes a picture of the human hand. The optical measuring apparatus then detects the registered feature part on the currently taken image, moves spectroscopic analyzer by moving mechanism, and projects measuring light onto the registered feature part.

14 Claims, 16 Drawing Sheets

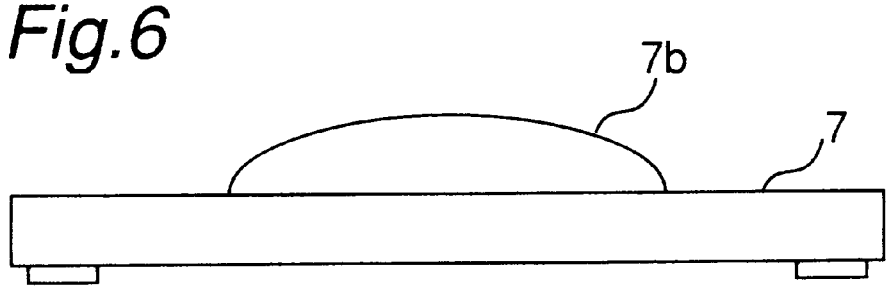
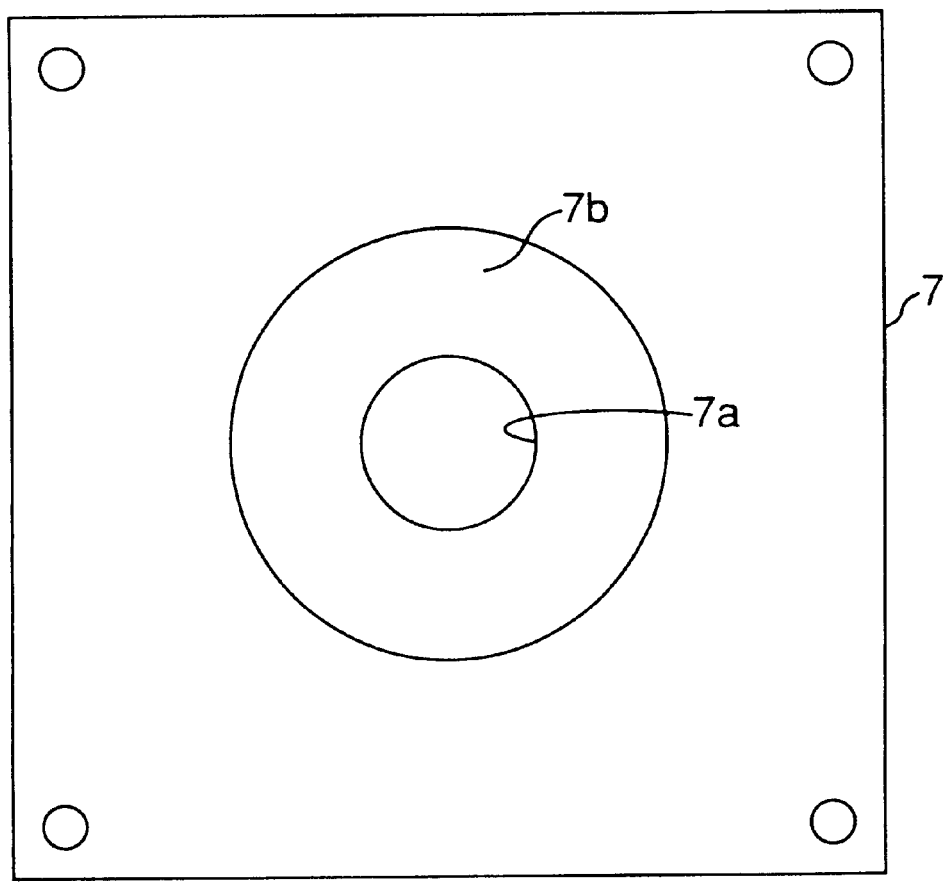

ial vein of a wrist is known. (See, for example, Japanese Pat. Hyo. Hei-5-508336). In this locating apparatus, two windows are formed a certain distance apart, and the superficial vein can be observed through these windows. The user mounts the locating apparatus on a wrist and sets the locating apparatus so that the vein should be at the center of both windows. Then the user marks the locations of the windows with a felt pen and the like. After removing the locating apparatus, the user sets the detection filters on the marked place.

METHOD AND APPARATUS FOR MEASURING CONCENTRATION BY LIGHT PROJECTION

FIELD OF THE INVENTION

The present invention relates to method and apparatus for performing a measurement at the same target part of a measured object in measuring the concentration of a particular component within the measured object using the transmittance or reflectance spectrum obtained by irradiating the measured object with light.

RELATED ART

In recent years, in the field of clinical examinations and the like, so-called noninvasive monitors that noninvasively measure the concentration of a particular component in urine, blood, or an organism have been studied. Procedures measuring the concentration of a particular component within an organism using such noninvasive monitors are classified into the types where light transmitted by the tissue of the organism is used and types where light reflected by the tissue of the organism is used. In a scattering system such as the tissue of an organism, the absolute value of absorbance cannot be obtained, and therefore, the concentration of the absorbing substance cannot be obtained, unless the effective length of the light path resulting in scattering and the light quantity incident on the measured object are determined. Further, the light quantity incident on the measured object is varied by the light directly reflected by the surface of the measured object and others, because conditions of the surface and the incident angle of the light are varied. Therefore, when measuring the concentration of a particular component within an organism using such noninvasive monitors, it is necessary to project and receive light each time at the same location of the measured object under fixed conditions.

The following kinds of such noninvasive monitors are known for locating the light projecting member and the light receiving member against the measuring part of an organism. One kind is a clipping type that holds the measuring part of an organism between a clipping member in which a luminescent element is imbedded and another clipping member in which a light receiving element is imbedded. The light receiving element receives the light emitted by the luminescent element and transmitted by the measuring part to determine the information about the organism based on the intensity of the received light. Another kind is an adhesive type that sticks the luminescent and light receiving elements to the measuring part with double-sided adhesive tape. As in the clipping type, the light receiving element receives the light emitted by the luminescent element and transmitted by the measuring part to determine the information about the organism based on the intensity of the received light. (See, for example, Japanese Pat. Kai. Hei-6-14906).

Another kind of known noninvasive monitor has a stand having a groove of a size that allows the groove to receive a finger. One side of the groove has an entrance for the light path and the other side has an exit for the light path, so that the length of the light path from the entrance to the exit is made constant regardless of the size and shape of the finger. Further, the stand may have a roller and a spring that generate pressure on the finger of a size within a particular range to concentrate the blood within the finger and to increase the amount of blood at the examined part. (See, for example, Japanese Pat. Hyo. Hei-6-503728).

Further, a locating apparatus for positioning the detection filters of the light sending and receiving members right over

DISCLOSURE OF THE INVENTION

Incidentally, in noninvasive measurement of the concentration of a particular component within an organism, the following factors and the like influence the reproducibility of measurements, in addition to environmental conditions:

Colors, shapes, changes in physiological states, and the combination of physiological functions, shown as feature differences, regional differences, and the like among measuring parts and within each individual measuring part.

Setting conditions due to the replacement of the measured object at each measurement, shown as errors in measuring methods.

The angle of the incident light incident on a location having a visual characteristic in the measuring part.

Changes in contact pressure between the measuring part and the measuring opening of the measuring member having a light projecting member and a light receiving member.

Examples of changes in measurements due to such measuring conditions are shown in FIGS. 13 to 15.

The measurement data in FIG. 13 was obtained as follows:

(1) Using an optical fiber, we projected light onto a previously selected measuring part of a patient's palm and received the reflected light to measure a reference energy spectrum (A).

(2) We projected light onto a location 1 mm apart from the previously selected part without changing the angle of irradiation to measure an energy spectrum (B).

(3) We projected light onto a location further 1 mm apart, that is, 2 mm apart from the previously selected part without changing the angle of irradiation to measure an energy spectrum (C).

(4) We let the patient drink a glucose tolerance test solution, Trelan 75, manufactured by Shimizu Pharmaceutical Co. At the time when the blood sugar of the patient changed to 15 mg/dl, we projected light onto the original location without changing the angle of irradiation to measure an energy spectrum (D).

(5) We divided the energy spectra (A), (B), (C), (D) by the energy spectrum (A) obtained in the step (1) and multiplied the results by 100 to obtain $$(E)=\{(A)/(A)\}\times 100, (F)=\{(B)/(A)\}\times 100,$$

$$(G)=\{(C)/(A)\}\times 100, (H)=\{(D)/(A)\}\times 100.$$

(6) Then we subtracted (E) from (F) to obtain the curve $h_1$ of FIG. 13. We subtracted (E) from (G) to obtain the curve $h_2$ of FIG. 13. We subtracted (E) from (H) to obtain the curve $h_3$ of FIG. 13.

FIG. 14 was obtained as follows:

Using an optical fiber, we projected light onto a previously selected measuring part of a patient's palm and received the reflected light to measure the reference energy spectrum (A). Then, corresponding to the above procedures (2) and (3), we measured the energy spectra by changing the angle of irradiation by 1, 2, 3 and 4 degrees instead of changing the location of the originally selected measuring part. Then, as in the above (4), at the time when the patient's blood sugar changed to 15 mg/dl after the patient had drunk the above glucose tolerance test solution, we measured an energy spectrum. Then, as in the above (5) and (6), we obtained the curves $h_{11}$, $h_{12}$, $h_{13}$, and $h_{14}$ of FIG. 14.

FIG. 15 was obtained as follows: We projected light onto a previously selected measuring part of a patient's palm and received the reflected light to measure a reference energy spectrum (A). Then corresponding to the above (2) and (3), we measured energy spectra by pressing the optical fiber to the measuring part by 1, 2, 3, and 4 mm to add pressure instead of changing the location of the measuring part or the angle of irradiation. Then, as in the above (4), at the time when the patient's blood sugar changed to 15 mg/dl after the patient had drunk the above glucose tolerance test solution, we measured an energy spectrum. Then, as in the above (5) and (6), we obtained the curves $h_{21}$, $h_{22}$, $h_{23}$, and $h_{24}$ of FIG. 15.

In FIGS. 13 to 15, at an absorption wavelength of glucose 1667 nm (6000 cm$^{-1}$) the energy spectrum changes by about 2.75% with the change in blood sugar to 15 mg/dl due to glucose. On the other hand, the energy spectrum changes by about 4.88% with the 1 mm dislocation of the measuring part. The energy spectrum changes by about 0.29% with the change of the angle of irradiation by 1 degree. The energy spectrum changes by about 2.89% with the application of pressure by the length 1 mm of the optical fiber. In actual cases of measuring the concentration of glucose within an organism, the resolution of 1 mg/dl is required, so that a change of 0.18% must be measured by conversion. Therefore, it is required that the precision for reproduction be less than about 0.04 mm for the location of the measuring part, about 0.62 degrees for the angle of irradiation, and about 0.66 mm in the length of the optical fiber for the pressure.

Incidentally, monitors using a probe of the clipping method for acquiring information about organisms minutely differ in shape and size. For the method of sticking a probe for the measurement of information about organisms to the measuring part of an organism using double-sided adhesive tape, it is difficult to paste the form for the measurement of information about organisms exactly onto an originally selected measuring part of an organism. Therefore, it is difficult for the prior clipping method and double-sided adhesive tape method to maintain the above precision for reproduction, as we see from the measurement data in FIGS. 13 to 15. As a result, there has been a problem that the measurement results are so dispersed that results having sound reproducibility cannot be obtained. Further, a monitor using a probe of the clipping method for acquiring information about organisms compresses a blood vessel and the like, when measuring the concentration of a particular component of an organism at its measuring part. Therefore, there has been a problem that the blood stream can be affected, so that stable measurements cannot be obtained.

Further, in a monitor using an apparatus for receiving a finger, the size of the groove is determined by the average of the measuring parts of numerous organisms. Therefore, there has been a problem that it is difficult to respond to differences in size due to individual differences in the measuring parts of organisms having various sizes. In addition, there is another problem. In order to make the measuring part of an organism completely identical each time, the second dimension (the depth of the inserted part) can be corrected, but the third dimension (the height and the angle of the inserted part and the rotation of the measuring part) is difficult to correct.

Further, in monitors using a locating apparatus, the users locate the measuring part with their eyes depending on the mark imprinted on the measuring part of an organism using a felt pen and the like. Therefore, if the marking disappears, then not only is the locating the measuring part impossible, but also the angle of the incident light with the measuring part of the organism and the contact pressure is different for each measurement. As a result, there has been a problem that a high degree of reproducibility is difficult to obtain.

An object of the present invention is therefore to provide a method of restoring the measuring location such that light is projected onto the measuring part of the measured object under constant measurement conditions. Another object of the present invention is an optical measuring apparatus that can obtain measurements of high reliability having small dispersion among repeated measurements.

SUMMARY OF THE INVENTION

The present invention projects measuring light onto a measured object and detects the spectral intensity of the light transmitted or reflected by the measured object to measure the concentration of a particular component within the measured object based on the spectral intensity, the present invention takes a picture of the measured object to display its image. Then the invention selects from the image a part that has a visually recognizable feature to mark the part and stores the marked image as a registered image. When restoring the measuring location, the present invention takes a picture of the measured object to compare the pattern of that image with the pattern of the registered image, detects the part on the taken image corresponding to the marked part of said registered image to determine the detected part as the measuring location for letting the measuring light incident thereon, and then executes the measurement.

When registering the measuring location, the present invention takes a picture of the measured object to select and mark a part that has a visually recognizable feature and stores the marked image as a registered image. When restoring the measuring location, the present invention takes a picture of the measured object to compare the pattern of that image with the pattern of the registered image, and detects the part corresponding to the marked part of the registered image to project the measuring light thereon.

The present invention also detects, by pattern recognition, the part corresponding to the marked part of the registered image, from the pattern of the image of the measured object taken during the restoration of the measuring location. The present invention detects, by pattern recognition, the part corresponding to the marked part of the registered image, from the pattern of the image of the measured object taken during the restoration of the measuring location.

The present invention also permits detection, with the human eye, of the part corresponding to the marked part of the registered image, from the pattern of the image of the measured object taken during the restoration of the measuring location. The present invention further permits detection with the human eye, if the part coinciding with the marked part or the registered image, from the pattern of the image of the measured object taken during the restoration of the measuring location.

The present invention also stores the marked image as a registered image together with information that identifies the measured object. The present invention identifies the measured object by the information stored with the registered image.

The present invention also detects, from the pattern of the image obtained from taking a picture of an organism, a part having a feature, and projects measuring light onto the detected part.

The present invention is further directed to a measuring apparatus having a projection optical system that projects measuring light onto a measured object. When detecting the spectral intensity of the light transmitted or reflected by the measured object to measure the concentration of a particular component within the measured object based on the spectral intensity, the measuring apparatus projects the measuring light onto a predetermined measuring location. The measuring apparatus is equipped with a measured-object mounting means that mounts the measured object, an image pickup means that takes a picture of the measured object, an image display means that displays the image of the measured object, an image registration means that during the registration of the measuring location, stores as a registered image an image in which a part having a visually recognized feature is marked by selecting the part from the pattern of the image of the measured object displayed on the image display means, a moving means that during the restoration of the measuring location, compares the pattern of the registered image with the pattern of the currently taken image of the measured object, identifies the location of the part corresponding to the marked part of the registered image, in the currently taken image of the measured object, and moves the projection optical system or the measured object mounting means so that the measuring light should be projected onto the identified part.

During the restoration of the measuring location, the measuring apparatus compares the pattern of the registered image with the pattern of the currently taken image of the measured object, detects the location of the part corresponding to the marked part of the registered image, in the currently taken image of the measured object, and moves the projection optical system or the measured object mounting means so that the measuring light should be projected onto the detected part.

In the present invention, the projection optical system or the measured object mounting means moves in the directions of X axis and Y axes that are orthogonal to a Z axis that is oriented in the direction of the optical axis of the measuring light. The projection optical system or the measured object mounting means moves in the directions of the X axis and Y axis that are orthogonal to the Z axis that is oriented in the direction of the optical axis of the measuring light.

In the present invention, the projection optical system moves in the direction of the Z axis.

In the present invention, the projection optical system rotates around the Z axis.

In the present invention, the measuring apparatus is equipped with a contact pressure sensor that detects contact pressure between the measured object and the measured object mounting means, a contact pressure memory that stores the output of the contact pressure sensor, and a pressurization device that reproduces the contact pressure stored in the contact pressure memory. During measurement, the measuring apparatus detects contact pressure between the measured object and the measured object mounting means and reproduces the contact pressure stored in the contact pressure memory.

In the present invention, the image registration means stores, as a registered image, the above marked image together with information that identifies the measured object. The measured object is identified by the information stored in the image registration means together with the registered image.

In the present invention, the measured object is an organism. The measuring apparatus moves the projection optical system or the measured object mounting means so that the measuring light should be incident on the part selected from the pattern of the image obtained from taking a picture of an organism.

The present invention is further directed to optical measuring apparatus having a projection optical system that projects measuring light onto a measured object. The optical measuring apparatus detects the spectral intensity of the light transmitted or reflected by the measured object to measure the concentration of a particular component within the measured object based on the spectral intensity. The optical measuring apparatus is equipped with a measured-object mounting means that mounts the measured object, an image pickup means that takes a picture of the measured object an image display means that displays the image of the measured object, an image registration means that during the registration of the measuring location, stores as a registered image an image in which a part having a visually recognized feature is marked by selecting the part from the pattern of the image of the measured object displayed on the image display means, a measuring location identifying means that during the restoration of the measuring location, compares the pattern of the registered image with the pattern of the currently taken image of the measured object, identifies the location of the part corresponding to the marked part of the registered image, in the currently taken image of the measured object, a moving means that moves the projection optical system so that the measuring light should be projected onto the part identified by the measuring location identifying means, a light receiving optical means that receives the light transmitted or reflected by the measuring part, a spectral intensity detecting means that detects the spectral intensity of the light transmitted or reflected by the measured object and received by the light receiving optical system, an arithmetic processing means that computes the concentration of a particular component within the measured object based on the spectral intensity, and an output means that outputs the concentration of the particular component.

During the restoration of the measuring location, the optical measuring apparatus compares the pattern of the registered image with the pattern of the currently taken image of the measured object, detects the location of the part corresponding to the marked part of the registered image, in the currently taken image of the measured object, and moves the projection optical system so that the measuring light should be projected onto the detected part. The optical measuring apparatus then receives the light transmitted or reflected by the measured object to detect the spectral intensity and detects the concentration of a particular component within the measured object based on the detected spectral intensity.

In the present invention, the projection optical system has an optical fiber. The measuring light is projected onto the selected part of the measured object through the optical fiber.

In the present invention, the light receiving optical system has an optical fiber. The light transmitted or reflected by the measured object is received through the optical fiber.

In the present invention, the light receiving optical system has an integrating sphere. The light transmitted or reflected by the measured object is collected by the integrating sphere.

In the present invention, the image registration means stores the marked image as a registered image together with information that identifies the measured object. The measured object is identified by the information stored in the image registration means together with a registered image.

In the present invention the measured object is an organism. The optical measuring apparatus moves the projection optical system or the measured object mounting means so that the measuring light should be incident on the part selected from the pattern of the taken image of an organism. The optical measuring apparatus then measures the concentration of a particular component within the organism.

BRIEF DESCRIPTION OF THE DRAWINGS

FIG. 6 is a front view of the transformation of a mounting base.

FIG. 7 is a top view of the mounting base in FIG. 6.

Embodiments of the present invention are described in the following, referring to the attached figures.

First Embodiment.

Figure 1:
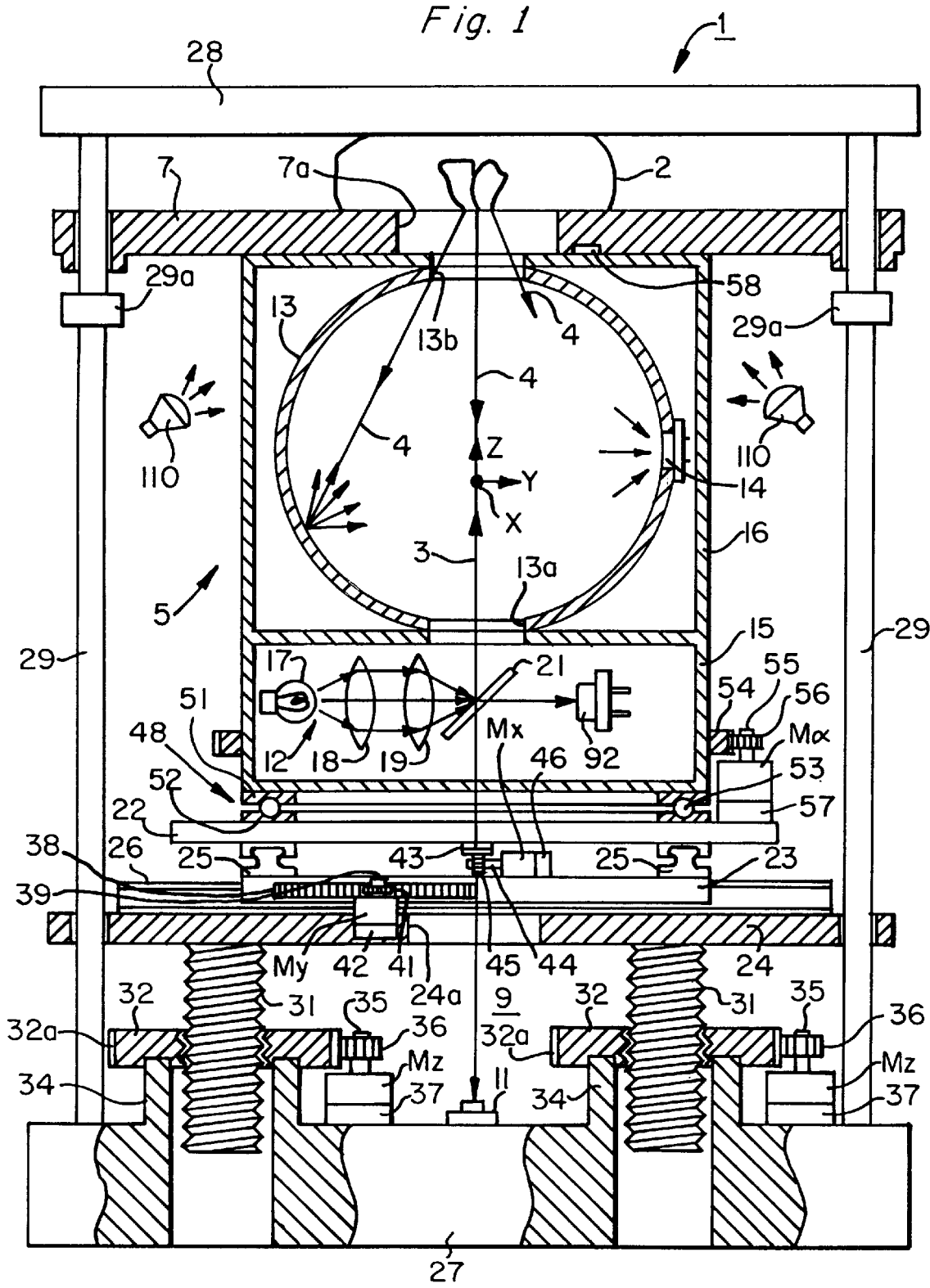
FIG. 1 is a diagram illustrating the construction of the spectroscopic analyzer and its moving mechanism of a first embodiment of optical measuring apparatus in accordance with the present invention.
Figure 2:
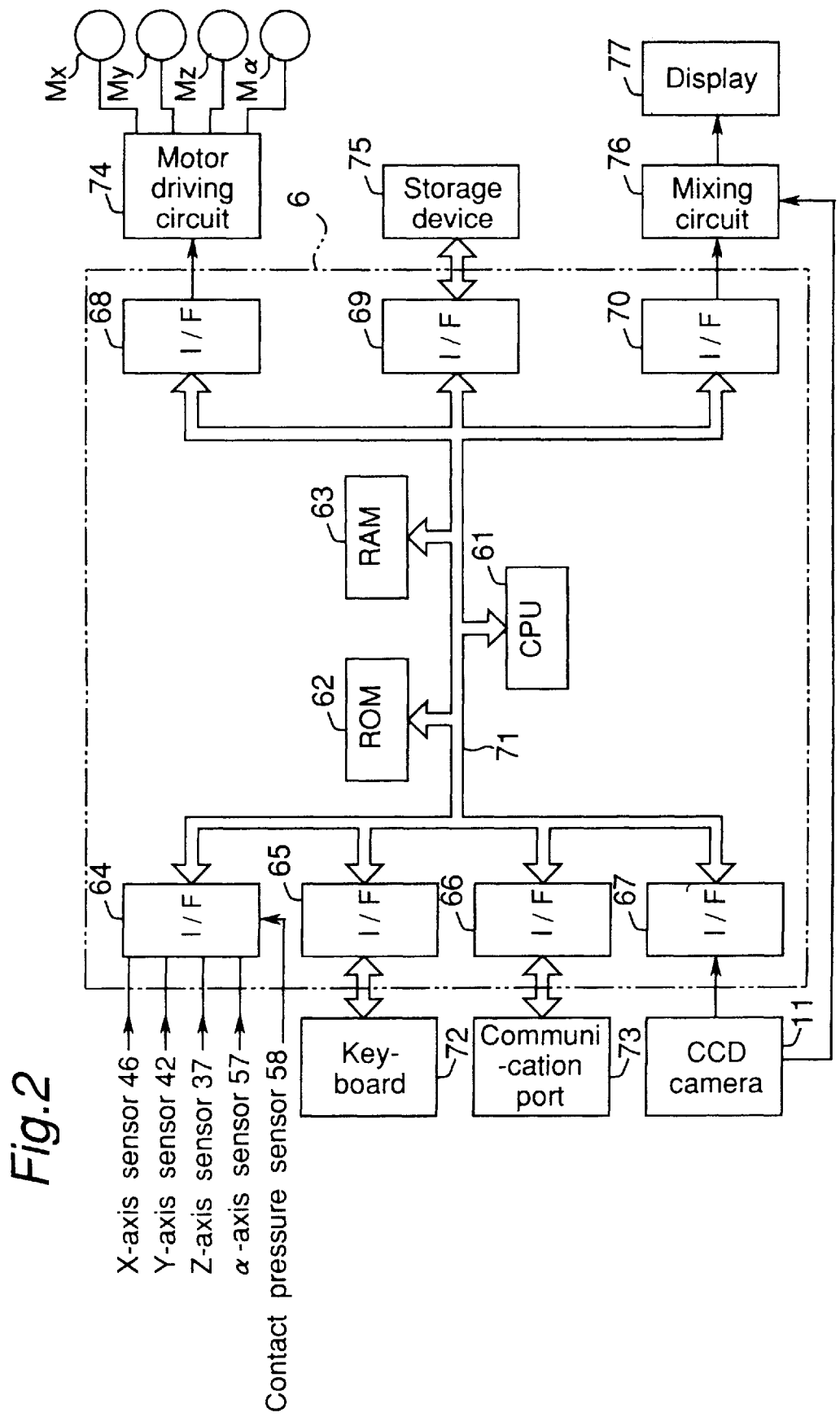
FIG. 2 is a block diagram illustrating the construction of the arithmetic and control processor of the moving mechanism in the optical measuring apparatus of FIG. 1.
Figure 3:
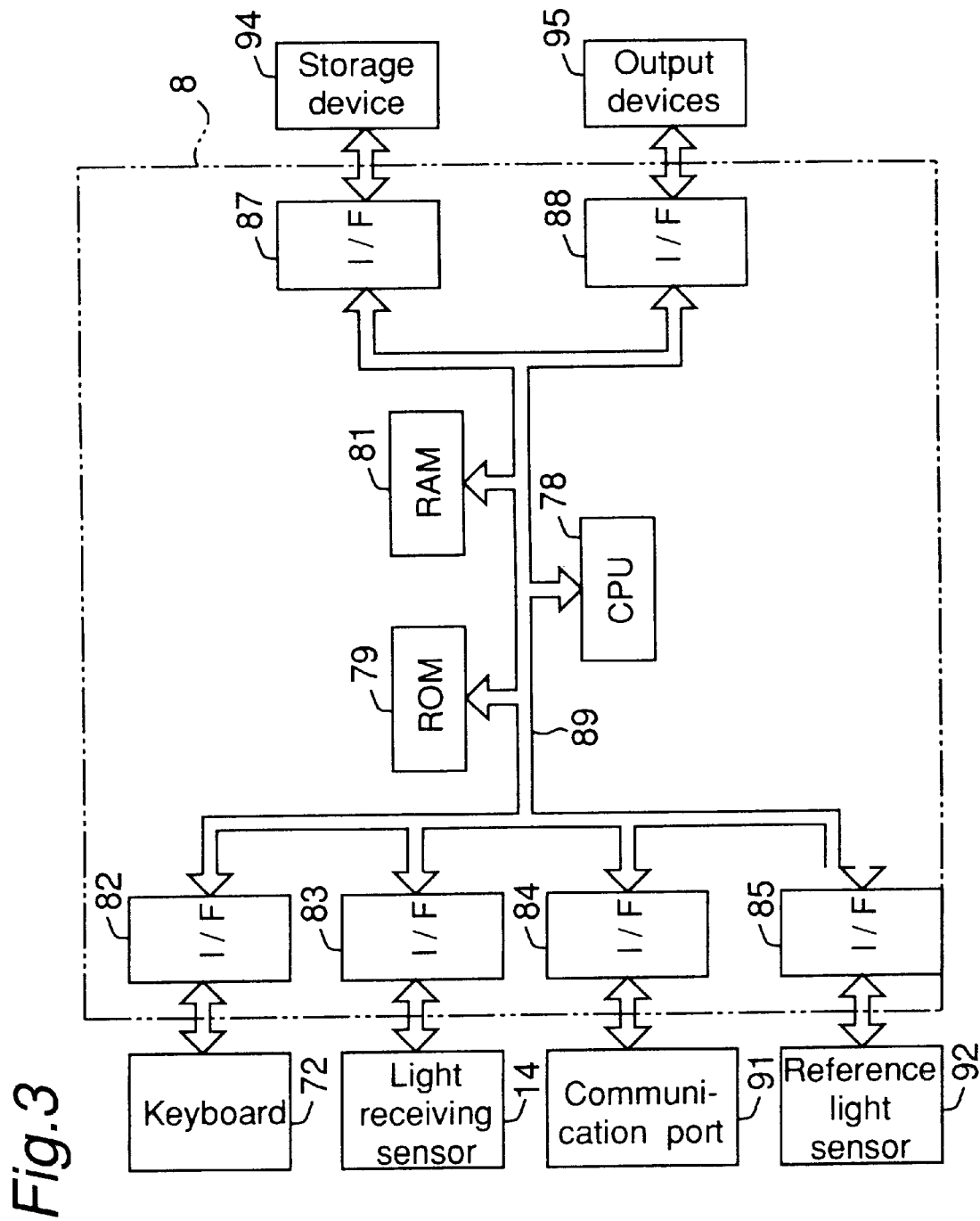
FIG. 3 is a block diagram illustrating the arithmetic processor of the spectroscopic analyzer in the optical measuring apparatus of FIG. 1.

FIGS. 1 to 3 illustrate the construction of an embodiment of optical measuring apparatus in accordance with the present invention. The optical measuring apparatus 1 is used for detecting the concentration of glucose from a human hand 2 that is the measured object. The optical measuring apparatus 1 is equipped with a spectroscopic analyzer 5 that projects measuring light 3 onto a human hand 2 to detect the spectral intensity of the reflected light 4, an arithmetic and control processor 6 (see FIG. 2) that controls the projecting location of the measuring light 3, an arithmetic processor 8 (see FIG. 3) that determines the glucose concentration based on the spectral intensity detected by the spectral analyzer 5, a moving mechanism 9 for the spectroscopic analyzer 5, and a CCD camera 11 (see FIGS. 1, 2) that takes a picture of the human hand 2 mounted on a mounting base 7.

The spectral analyzer 5 is equipped with a projection optical system 12 that projects measuring light 3 onto the human hand 2 mounted on the mounting base 7 for the measured object, an integrating sphere 13 that collects the light 4 projected by the projection optical system 12 and reflected by the human hand 2, and a light receiving sensor 14 that detects the intensity of the reflected light 4 collected by the integrating sphere 13. The projection optical system 12 is housed in a lower compartment 15 of spectroscopic-analyzer 5. The integrating sphere 13 is housed in an upper compartment 16 of spectroscopic analyzer 5.

The projection optical system 12 includes a light source 17, a collimator lens 18 that makes the light from the light source 17 parallel, a condenser lens 19 that condenses the parallel light emitted from the collimator lens 18, and a half mirror 21. The light source 17, collimator lens 18, and condenser lens 19 are set on the same optical axis. The half mirror 21 is set at an angle of 45 degrees with the optical axis. In this setting, the light emitted from light source 17 is reflected by the half mirror 21 in the direction having an angle 90 degrees with the optical axis. The measuring light is projected onto the human hand 2 through transmittance openings 13a, 13b formed on the integrating sphere 13 set on the upper side of the projection optical system 12 and a transmittance opening 7a formed on mounting base 7 set on the upper compartment 16. The light receiving sensor 14 is attached to integrating sphere 13 with its light receiving face directed toward the inside of the sphere. After being reflected by the human hand 2, the measuring light is collected by the integrating sphere and made incident on the light receiving sensor 14.

In the lower compartment 15 of the spectroscopic analyzer 5 is also set a reference light sensor 92 that detects the intensity of the light emitted from light source 17 of the projection optical system 12. The reference light sensor 92 is set opposite to the light source 17 from half mirror 21 of the projection optical system 12. The light emitted from the light source 17 is made incident on the reference light sensor 92 after being transmitted by half mirror 21.

The moving mechanism 9 for spectroscopic analyzer 5 is set under the lower compartment 15 of spectroscopic analyzer 5. The moving mechanism 9 supports the spectroscopic analyzer 5 so that the latter can move in the direction of the X axis that is vertical to the paper surface of FIG. 5 and in the direction of Y axis that is vertical to both the X axis and the Z axis that is oriented in the direction of the light path of the measuring light 3. The moving mechanism 9 supports spectroscopic analyzer 5 so that the latter can rotate around the Z axis. The moving mechanism 9 is equipped with an X-axis moving table 22, a Y-axis moving table 23, and a Z-axis moving table 24. The X-axis moving table 22 is supported by an X-axis rail 25 on the Y-axis moving table 23 so that the X-axis moving table can move in the direction of the X axis. The Y-axis moving table 23 is supported by a Y-axis rail 26 on the Z-axis moving table 24 so that the Y-axis moving table 23 can move in the direction of the Y axis. Further, the Z-axis moving table 24 is directed by a binding member 29 that binds to a base 27 of spectroscopic analyzer 5 a pressing member 28 that presses the human hand 2 so that the Z-axis moving table 24 can rise from the corners of the base 27, which has a rectangular shape, and can move in the direction of the Z-axis.

CCD camera 11 is set on the base 27. The CCD camera 11 is set so that when the spectroscopic analyzer 5 escapes from under the transmittance opening 7a by the moving mechanism 9 to an initial position, the optical axis of the CCD camera 11 should line up with the optical axis of the measuring light 3 in the spectroscopic analyzer 5. By this setting, when the spectroscopic analyzer 5 escapes from under the transmittance opening 7a by the moving mechanism 9, CCD camera 11 can direct its optical axis toward the human hand 2 illuminated by illuminating lamps 110 for pickup through transmittance openings 7a, 24a.

The 2-axis moving table 24 is supported by screw shafts 31 that project downward from its lower surface, nuts 32 that mesh with screw shafts 31, and nuts supporting members 34 that rise from the base 27 and support the nuts 32 on the top so that nuts 32 can rotate. The teeth 32a formed on the circumferences of nuts 32 mesh with pinions 36 that are attached to the output shafts 35 of Z-axis driving motors Mz. Therefore, when the Z-axis driving motors Mz rotate, then nuts 32 are rotated through pinions 36, so that screw shafts 31 move in the direction of their own axes. Therefore, the Z-axis moving table 24 moves in the direction of the Z axis. The amount of the movement of the Z-axis moving table 24 in the direction of the Z axis is detected by revolution sensors 37 of revolutions (called Z-axis sensors hereafter) installed in the Z-axis driving motors Mz.

On the Z-axis moving table 24 are fixed Y-axis rails 26. The Y-axis moving table 23 is supported on the Z-axis moving table by the Y-axis rails 26 so that the Y-axis moving table 23 can freely move in the direction of the Y axis. Racks 38 are attached to the sides of the Y-axis moving table 23. Pinions 41 attached to the output shafts 39 of the Y-axis driving motors My mesh with the racks 38. By these means, when the Y-axis driving motors My rotate, the Y-axis moving table 23 moves in the direction of the Y axis by power transmission through pinions 41 and racks 38. The amount of the movement of the Y-axis moving table 23 in the direction of the Y axis is detected by revolution sensors 42 (called Y-axis sensors hereafter) installed in the Y-axis driving motors My.

On the Y-axis moving table 23 are fixed X-axis rails 25. The X-axis moving table 22 is supported on the Y-axis moving table 23 by the X-axis rails 25 so that the X-axis moving table 22 can freely move in the direction of the X axis. A rack 43 is attached to the underside of the X-axis moving table 22. A pinion 45 attached to the output shaft 44 of an X-axis driving motor Mx meshes with the rack 43. By these means, when the X-axis driving motor Mx rotates, the X-axis moving table 23 moves in the direction of the X-axis by power transmission through pinions 45 and rack 43. The amount of the movement of the X-axis moving table 23 in the direction of the X axis is detected by a revolution sensor 46 (called X-axis sensor hereafter) installed in the X-axis driving motor Mx.

Between the X-axis moving table 22 and the lower compartment 15 of spectroscopic analyzer 5 is installed a rotary supporting mechanism 48 that supports the cylindrical lower compartment 15 and the upper compartment 16 of spectroscopic analyzer 5 so that they can rotate around their axis. The rotary supporting mechanism 48 includes directing members 51, 52 of a ring shape and ball bearings 53 that are inserted into circular grooves formed on the directing members 51, 52. A rack 54 is attached to the circumference of the lower compartment 15. A pinion 56 attached to the output shaft 55 of an α-axis driving motor Mα meshes with the rack 54. By these means, when the α-axis driving motor Mα rotates, the lower compartment 15 and upper compartment 16 of the spectroscopic analyzer 5 rotates around the Z-axis by power transmission through pinion 56 and rack 54. The amount of the rotation of the spectroscopic analyzer 5 is detected by a revolution sensor 57 (called α-axis sensor) installed in the α-axis driving motor Mα.

The mounting base 7 that mounts the human hand 2 on itself is a simple plane having in its center the transmittance opening 7a for transmitting the measuring light 3. A contact pressure sensor 58 is fixed on the mounting base 7 opposite to the upper compartment 16 of the spectroscopic analyzer 5. The contact pressure sensor 58 generates a contact pressure signal corresponding to contact pressure between the human hand 2 and mounting base 7 as follows. The spectroscopic analyzer 5 moves up in the direction of the Z axis, so that the upper compartment 16 of the spectroscopic analyzer contacts the mounting base 7 that is stopped by contacting a stopper 29a formed on the binding member 29. Then the spectroscopic analyzer 5 further moves up together with the mounting base 7 in the direction of the Z-axis. When the human hand 2 contacts the pressing member 28, the contact pressure sensor 58 generates the contact pressure signal. As illustrated in FIGS. 6 and 7, a protrusion 7b may be formed on the mounting base 7 to facilitate the locating of the human hand 2.

Arithmetic and control processor 6 may be a microcomputer, which includes a central processing unit (written CPU hereafter) 61, a read-only memory (written ROM hereafter) 62, a read/write memory (written RAM hereafter) 63, and interface circuits 64 to 70. The CPU 61 is connected to ROM 62, RAM 63, and interface circuits 64 to 70 through a bus 71.

Interface circuit 64 receives from X-axis sensor 46 an X-axis position signal of the X-axis moving table 22, from Y-axis sensor 42 a Y-axis position signal of the Y-axis moving table 23, from Z-axis sensor 37 a Z-axis position signal of the Z-axis moving table 24, from α-axis sensor 57 an α-axis rotary position signal, and from contact pressure sensor 58 a contact pressure signal. Interface circuit 65 receives from an operator key board 72 operator instruction signals necessary for interface circuit 65 corresponding to the operational contents of the keyboard input. Interface circuit 66 is connected to a communication port 73 for communication with the arithmetic processor 8 of FIG. 3. Interface circuit 67 is connected to CCD camera 11. Interface circuit 68 is connected to a motor driving circuit 74. The motor driving circuit 74 is connected to the X-axis driving motor Mx, Y-axis driving motors My, Z-axis driving motors Mz, and α-axis driving motor Mα described above with reference to FIG. 1. Further Interface circuit 69 is connected to a storage device 75 such as a hard disk. Interface circuit 70 outputs into a mixing circuit 76 an image signal of the human hand 2 that has been registered before. The mixing circuit 76 mixes a video signal output from the CCD camera 11 and the image signal of the registered human hand 2 to output the resulting signal into a display 77.

The arithmetic processor 8 of the spectroscopic analyzer 5 may be in a microcomputer, which includes a CPU 78, ROM 79, RAM 81 interface circuits 82 to 85, and interface circuits 87, 88. The CPU 78 is connected to the ROM 79, RAM 81, interface circuits 82 to 85, and interface circuits 87, 88 through a bus 89. The interface circuit 82 is connected to the keyboard 72 described above with reference to FIG. 2. Interface circuit 83 receives, from the light receiving sensor 14 described above with reference to FIG. 1, a spectral intensity signal of the reflected light 4 of measuring light 3 reflected by the human hand 2. Further, interface circuit 84 is connected to a communication port 91 for communication with the arithmetic and control processor 6 of FIG. 2. Interface circuit 85 receives from the reference light sensor 92 a reference light signal as a reference signal. The reference light signal corresponds to the luminous intensity of light source 17 in the projection optical system 12 of spectroscopic analyzer 5 described above with reference to FIG. 1. Interface circuit 87 is connected to storage device 94 such as a hard disk. Interface circuit 88 is connected to output devices 95 such as a printer and CRT display.

The construction of the location restoring apparatus of the optical measuring apparatus 1 has been described so far. Next, referring to the flowcharts of FIGS. 8 to 10, the operation of the optical measuring apparatus 1 equipped with the location restoring apparatus is described together with a method of restoring the measuring location for a preselected location of the human hand 2.

Registration Mode of the Measuring Location

Figure 8:
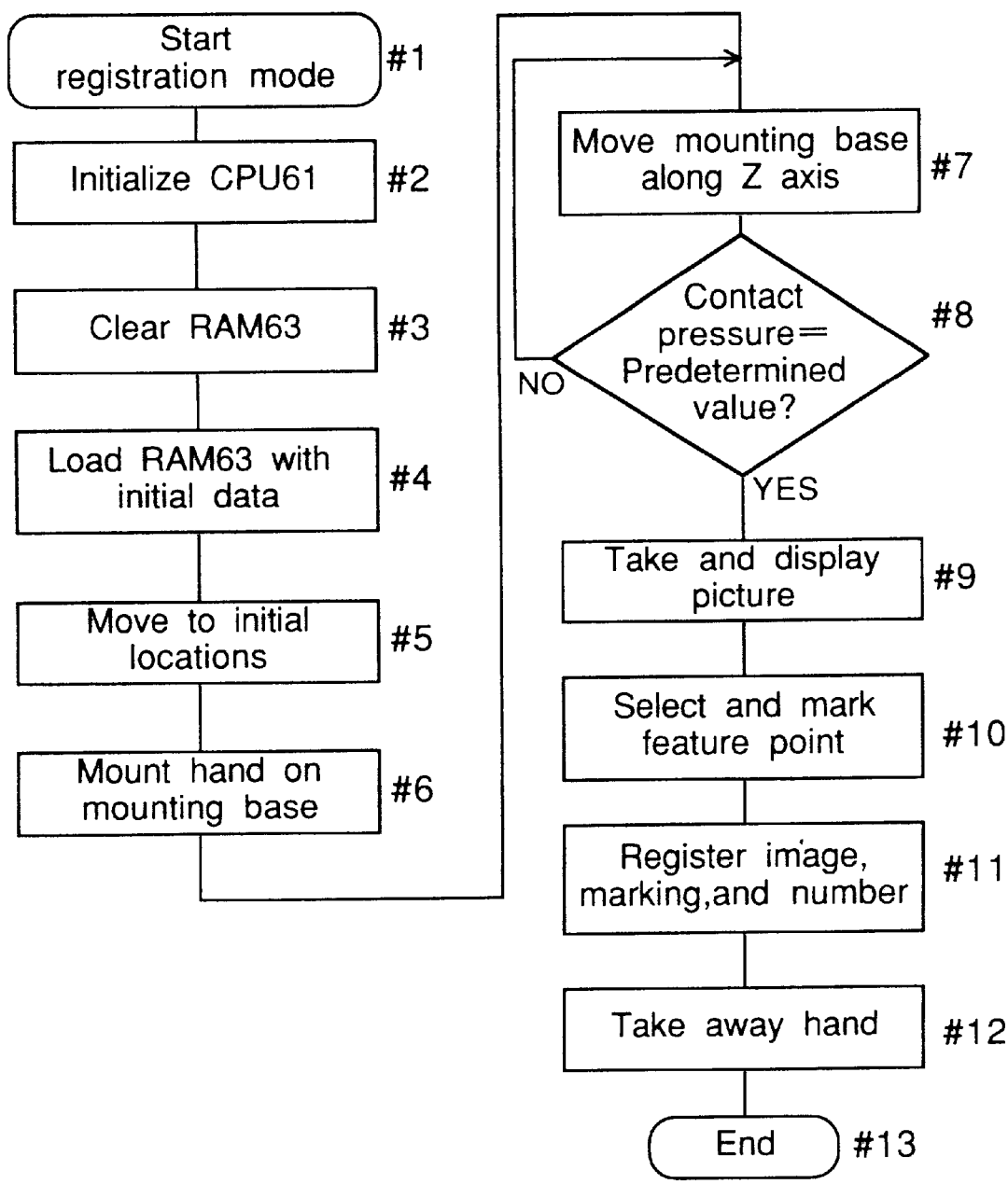
FIG. 8 is a flowchart of the registration mode.

When the power supply of optical measuring apparatus 1 is turned on, and the operator selects the registration mode for the measuring location to give an instruction for starting the registration mode for the measuring location through keyboard 72, the registration routine for the measuring location illustrated in FIG. 8 starts (#1). Then CPU 61 of arithmetic and control processor 6 is initialized (#2), and RAM 63 is cleared (#3).

After that, CPU 61 of arithmetic and control processor 6 loads RAM 63 through interface circuit 69 with the initial data for X-axis moving table 22, Y-axis moving table 23, Z-axis moving table 24, and the angle of α-axis rotation that is stored in storage device 75 (#4). These X-axis moving table 22, Y-axis moving table 23, Z-axis moving table 24, and the angle of α-axis rotation are moved to their initial locations (#5).

The human hand 2 is mounted on mounting base 7 (#6). Mounting base 7 is moved in the direction of the Z axis toward the pressing member 28 (#7). When the human hand contacts pressing member 28, and contact pressure sensor 58 gives a predetermined value, the mounting base 7 is stopped (#8). In this state, CCD camera 11 takes a picture of the human hand 2 to display its image on display 77 (#9). An example of the displayed image on display 77 is illustrated in FIG. 4.

In the pattern formed by curves 96, 97, and 98 in the displayed image of the palm of the human hand 2 displayed on display 77, the operator selects a visually recognized feature point P with a pointing device such as a trackball accompanied with keyboard 72 to display the feature point P with the symbol x (#10). Here, referring to FIG. 1, the center point $P_0$ of the displayed image corresponds to the origin of the X-Y plane where the X axis and Y axis intersect each other.

Figure 4:
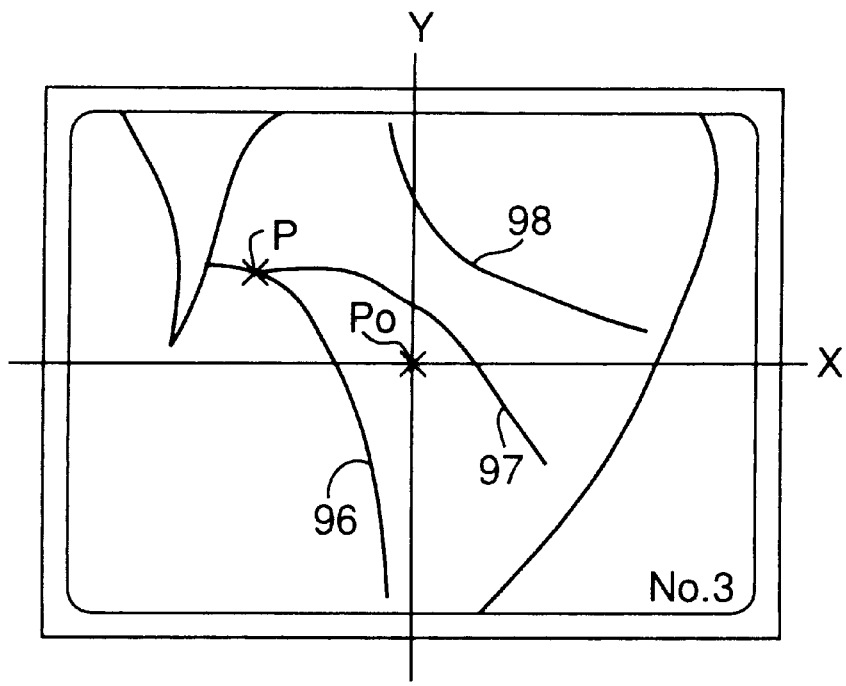
FIG. 4 is a diagram illustrating a registered image of a feature part in the registration mode.

The above pattern of the displayed image is stored in storage device 75 together with the symbol x marked on the feature point P, the contact pressure signal output from contact pressure sensor 58, and a registration number that identifies the human hand 2, say No. 3 as shown in FIG. 4 (#11). After that, mounting base 7 goes down, and the human hand 2 is taken away from mounting base 7 (#12). Then the registration mode is terminated (#13).

Blood Sugar Measurement Mode

Figure 9:
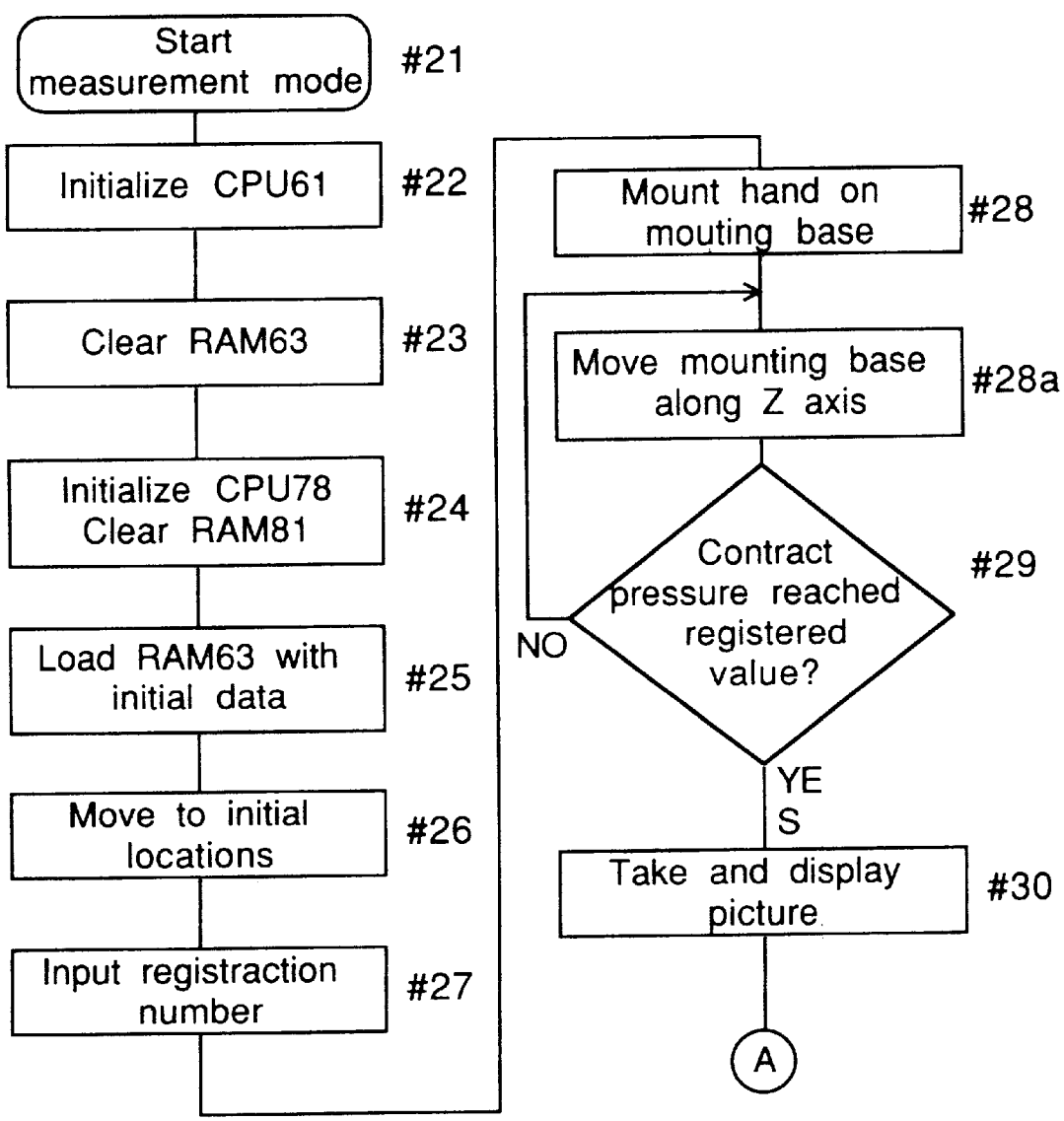
FIG. 9 is a flowchart of the measurement mode.
Figure 10:
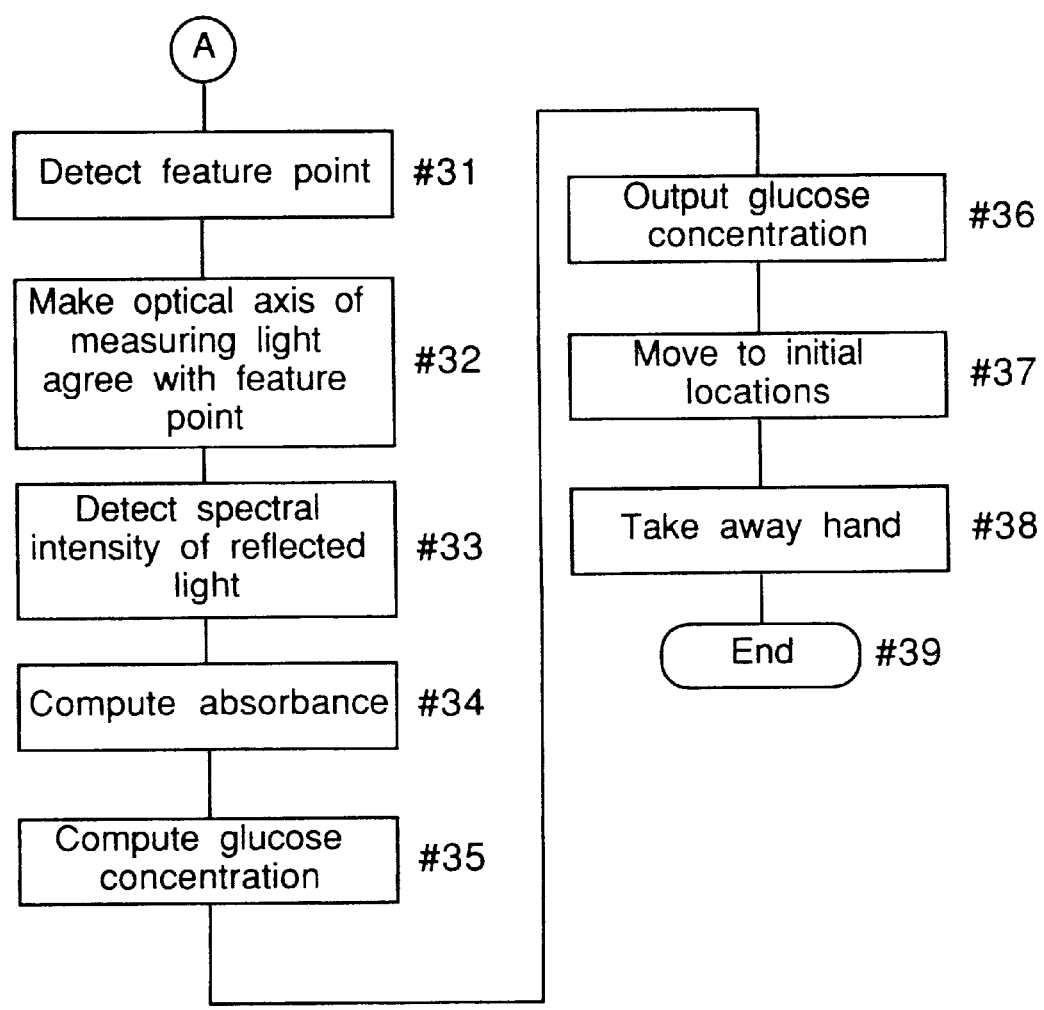
FIG. 10 is a flowchart of the measurement mode.

In the measuring routine illustrated in FIGS. 9 and 10, when the power supply of optical measuring apparatus 1 is turned on, and the operator selects the measurement mode to give an instruction for starting measurement through keyboard 72, the measurement routine starts (#21). Then CPU 61 of arithmetic and control processor 6 is initialized (#22), and RAM 63 is cleared (#23). Next, CPU 78 of arithmetic processor 8 in spectroscopic analyzer 5 is initialized, and RAM 81 is cleared (#24).

After that, CPU 61 of arithmetic and control processor 6 loads RAM 63 through interface circuit 69 with the initial data of X-axis moving table 22, Y-axis moving table 23, Z-axis moving table 24, and the angle of α-axis rotation that are stored in storage device 75 (#25). These X-axis moving table 22, Y-axis moving table 23, Z-axis moving table 24, and the angle of α-axis rotation are moved to their initial locations based on the initial data (#26).

After the registration number of a patient who has been registered in the registration mode to measure the glucose concentration, say No. 3, is input through keyboard 72 (#27), the human hand 2 of the registration No. 3 is mounted on the mounting base 7 (#28). Next, the Z-axis moving table 24 is moved up in the direction of the Z-axis until the human hand contacts the pressing member 28, and the contact pressure between human hand 2 and mounting base 7 output from contact pressure sensor 58 becomes the value registered in the registration mode (#28a and #29).

Figure 5:
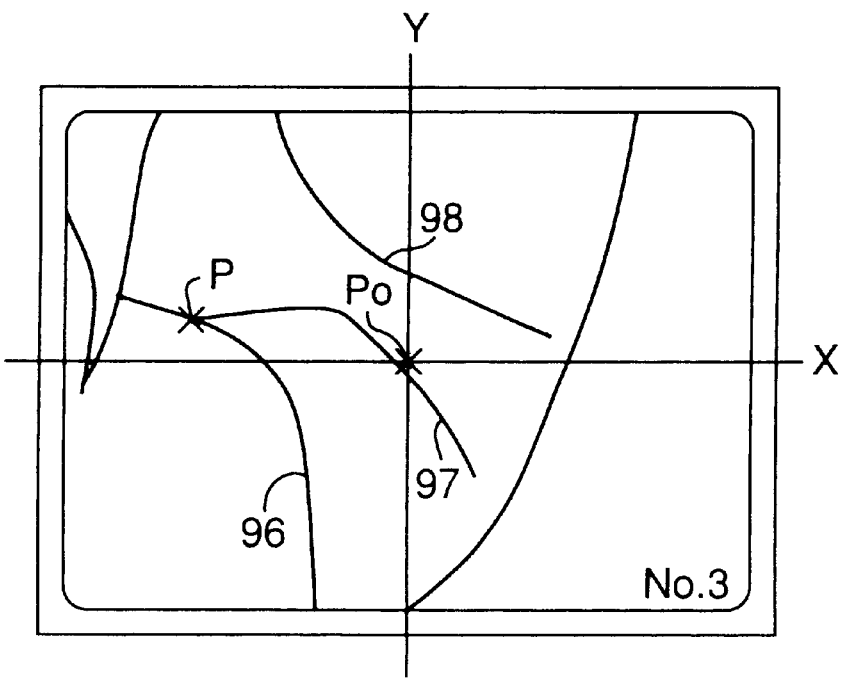
FIG. 5 is a diagram illustrating the decision of a feature part in the measurement mode.

When the Z-axis moving table 24 stops, CCD camera 11 displays the video signal of the palm of the human hand 2 on display 77 through mixing circuit 76 (#30). An example of the image displayed on the display 77 at this time is illustrated in FIG. 5. The CPU 61 of arithmetic and control processor 6 takes in the image signal of the palm of the human hand 2 output from CCD camera 11 to perform image processing. By means of pattern recognition, CPU 61 compares the pattern of the taken image of the palm of the human hand 2 with the image pattern of the palm of the human hand 2, No. 3, registered in the registration mode, and detects the feature point P registered in the registration mode from the image pattern of the palm of the human hand 2, No. 3, currently displayed on display 77 (#31).

Alternatively, the feature point P may be detected from the image of the palm of the human hand 2, No. 3, currently displayed on display 77 by the operator with his or her eyes as follows. The image signal of the palm of the human hand 2, No. 3, currently displayed on display 77 is mixed with the image signal of the palm of the human hand 2, No. 3, registered in the registration mode by mixing circuit 76, and both images are superimposed over each other on the display 77. Then the operators can detect with their eyes the feature point P registered in the registration mode, in the current image of the palm of the human hand 2, No. 3. The software for pattern recognition becomes unnecessary in this way, so that the manufacturing costs for developing measurement software for the optical measuring apparatus can be cut down.

After detecting the feature point P from the image pattern of the palm of the human hand 2 currently displayed on the display 77, CPU 61 of arithmetic and control processor 6 moves X-axis moving table 22 and Y-axis moving table 23 in the directions of the X axis and the Y axis respectively, to make the optical axis of the measuring light of spectroscopic analyzer 5 agree with the detected feature point P (#32). At this time, the arithmetic and control processor 6 monitors the incident spot diameter of the measuring light 3 incident on the human hand 2 with display 77 and corrects the incident spot diameter by rotating spectroscopic analyzer 5 around the Z- axis with the α-axis driving motor Mα.

By the above steps #21 to #32, the location of spectroscopic analyzer 5 is determined so that the measuring light 3 should be incident on the registered feature point P of the palm of the human hand 2. Then CPU 61 of arithmetic and control processor 6 outputs a spectrometry starting signal to CPU 78 of arithmetic processor 8 in spectroscopic analyzer 5 through the interface circuit 66, communication port 73 and through the communication port 91 and interface circuit 84 of arithmetic processor 8 (#33). When CPU 78 of arithmetic processor 8 in spectroscopic analyzer 5 receives the spectrometry starting signal from CPU 61 of arithmetic and control processor 6, CPU 78 executes the computation of the absorbance for the palm of the human hand 2 based on the spectral intensity signal of the reflected light 4 reflected from the feature point P of the palm of the human hand 2 and output from light receiving sensor 14 and the spectral intensity of light source 17 output from reference light sensor 92 (#34). Next, CPU 78 executes the computation of the glucose concentration based on the results of the absorbance computation (#35) to output the obtained glucose concentration into output devices 95 (#36)

After that, CPU 78 of arithmetic processor 8 outputs to CPU 61 of arithmetic and control processor 6 a measurement termination signal for glucose concentration through the interface circuit 84 and communication port 91 and through the communication port 73 and interface circuit 66 of arithmetic and control processor 6. When receiving the measurement termination signal, CPU 61 of arithmetic and control processor 6 moves X-axis moving table 22, Y-axis moving table 23 and Z-axis moving table 24 to their initial locations (#37). Then the human hand 2, No. 3 is taken away from mounting base 7 (#38), and a first measurement of glucose concentration is completed (#39). The subsequent measurements of glucose concentration on and after a second time are conducted following the steps 21 to #39.

As described above, the present embodiment sets the human hand 2 on the measured object mounting base 7 of spectroscopic analyzer 5 and takes a picture of the measured object with a camera to select the measuring point P having a feature from the pattern of the image, so that the present embodiment can make the measuring light 3 incident on the measuring point P at each measuring time after that. By this means, when measuring glucose concentration by detecting the reflected light 4 of the measuring light 3 projected onto the human hand 2, the present embodiment can greatly improve the reproducibility for the measuring location and lower the dispersion of the measurements due to changes in the measuring location.

Figure 16:
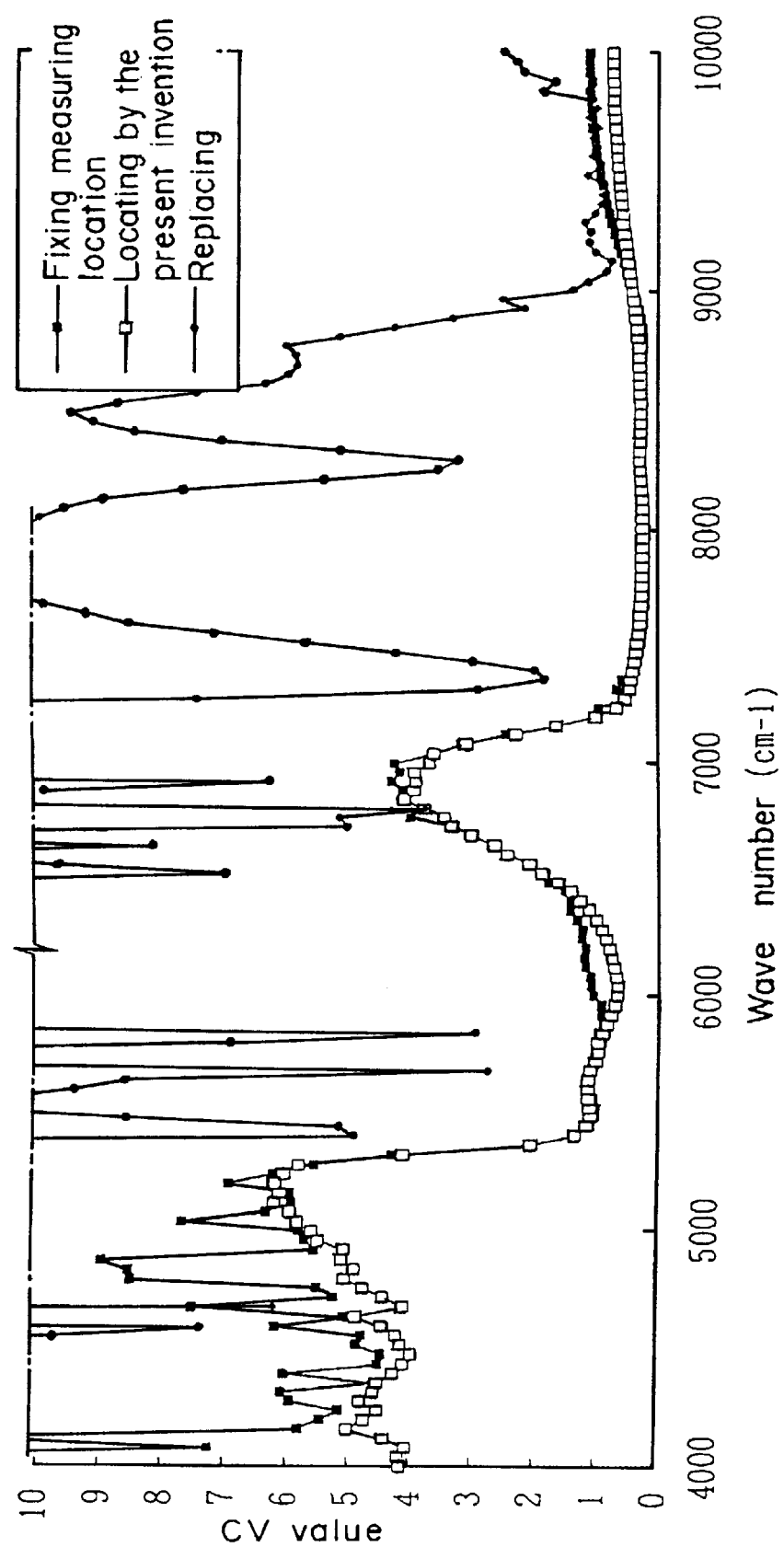
FIG. 16 is a graph illustrating the CV values of measured spectra obtained from using a spectrometric apparatus in accordance with the present invention. In the figure, ■ indicates the measurements obtained from fixing the location by a spectrometric apparatus of the present invention; □ indicates the measurements obtained from setting the location according to a method of the present invention; and ♦ indicates the measurements obtained from replacement without using the present invention.
Figure 17:
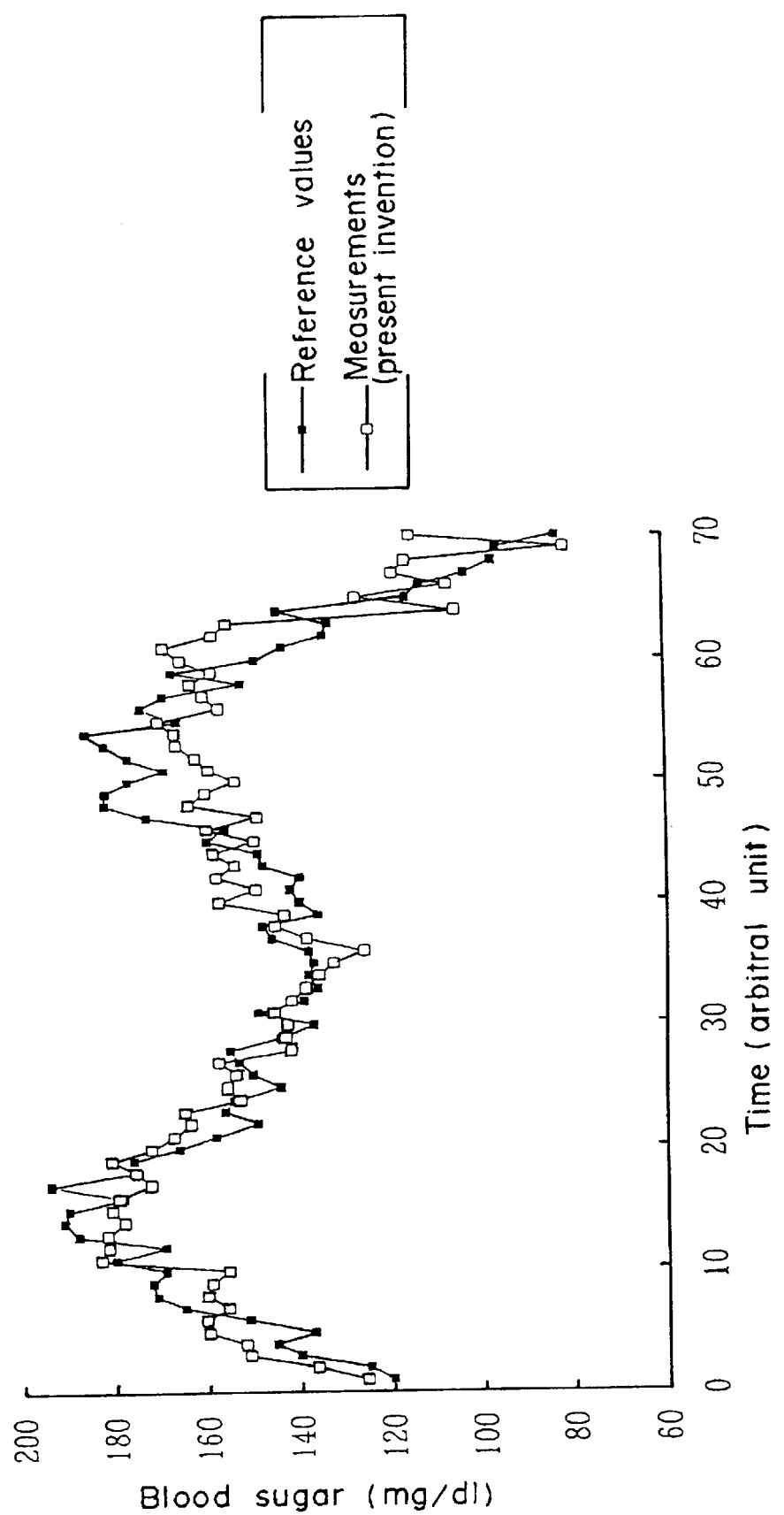
FIG. 17 is a graph illustrating temporal changes in blood sugar. In the figure, ■ indicates reference values (measured by drawing blood); and □ indicates values obtained from fixing the measuring location by a spectrometric apparatus of the present invention.
Figure 18:
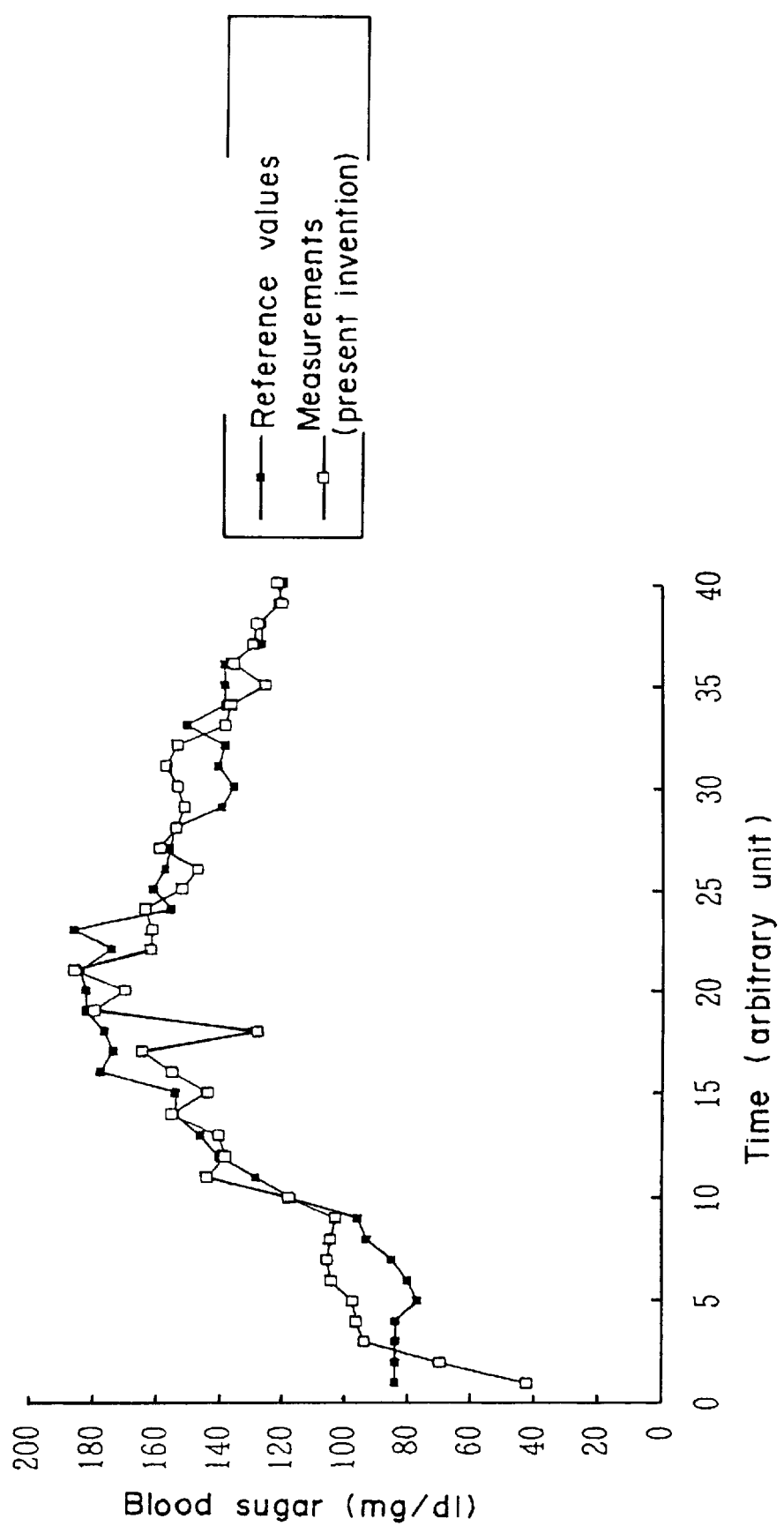
FIG. 18 is a graph illustrating temporal changes in blood sugar. In the figure, ■ indicates reference values (measured by drawing blood); and □ indicates values obtained from determining the measuring location according to a method of the present invention.

FIGS. 16, 17, and 18 illustrate some results obtained by the measurement using a measuring apparatus of the present embodiment in accordance with the present invention. FIG. 16 illustrates the CV values (%), that is, (standard deviation/average)×100 (%), of three kinds of spectra obtained from a human hand. The figure shows that the measurements indicated by ■ and obtained from fixing the location agree extremely well with the measurements indicated by □ and obtained from setting the location according to the method of the present invention. In contrast, the measurements obtained from simple replacement without using the present invention greatly depart from the measurements obtained from fixing the location.

FIG. 17 illustrates temporal changes in blood sugar in a case where we let the patient drink a glucose tolerance test solution, Trelan 75, manufactured by Shimizu Pharmaceutical Co. The figure shows that the measurements for a human hand soundly agree with reference values (blood sugar measured by drawing blood).

Further, FIG. 18 illustrates the measurement results obtained from determining the measuring location following the present invention from the registered image and the currently taken image. The measurement results indicated by □ agree extremely well with reference values indicated by ■. The data indicated by represents the expected values obtained by a publicly-known computer simulation and greatly shifts from the reference values compared with the measurement results due to the present invention.

Second Embodiment.

Figure 11:
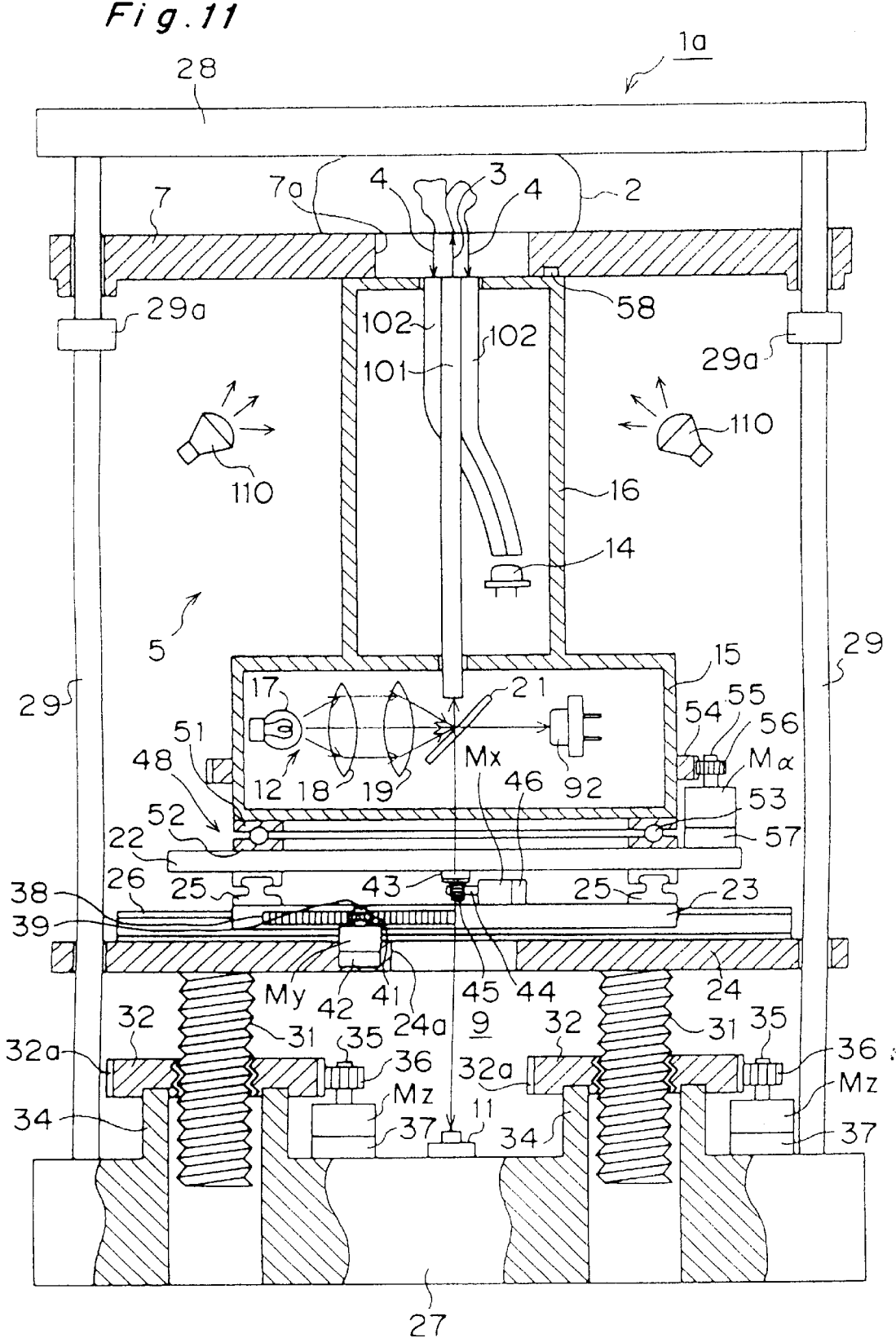
FIG. 11 is a diagram illustrating the construction of the spectroscopic analyzer and its moving mechanism of a second embodiment of optical measuring apparatus in accordance with the present invention.

FIG. 11 illustrates the optical measuring apparatus of a second embodiment in accordance with the present invention. The optical measuring apparatus 1a projects the light of the projection optical system 12 onto the human hand 2 set on the mounting base 7, in the optical measuring apparatus 1 of the first embodiment, through an optical fiber 101, and directs the reflected light 4 reflected by the human hand 2, in place of the integrating sphere 13 of the measuring apparatus 1 of FIG. 1, through an optical fiber 102 into the light receiving sensor 14. The construction of the part other than the optical fibers 101, 102 is the same as the corresponding part of the optical measuring apparatus 1 described with reference to FIG. 1. Therefore, in FIG. 11, the components corresponding to those in FIG. 1 are denoted by the same numerals, and redundant descriptions are omitted.

According to this construction, the shape of the optical measuring apparatus 1a becomes compact by the use of optical fibers 101, 102. The construction becomes simple. The handling of the apparatus becomes easier.

Third Embodiment.

Figure 12:
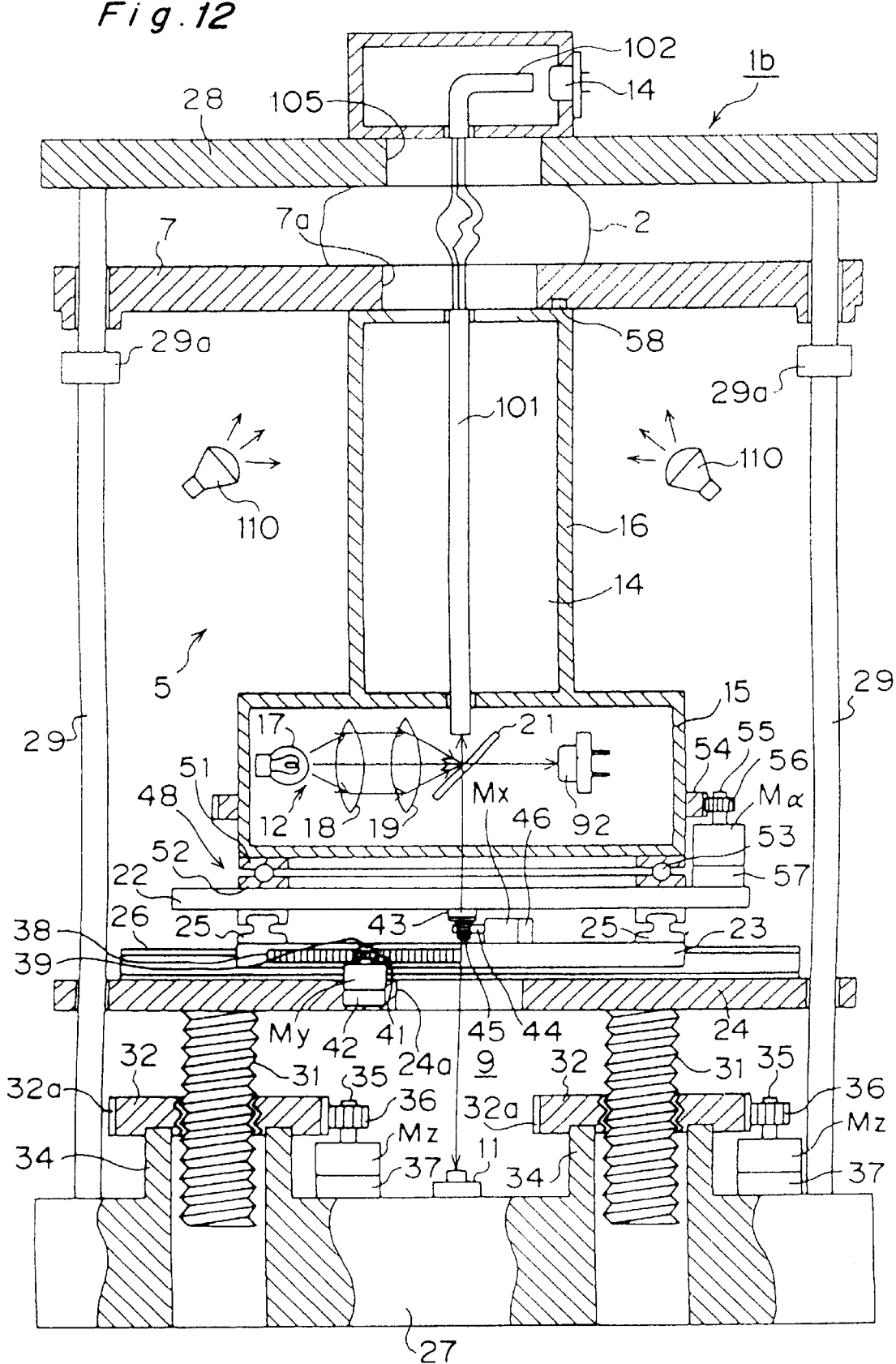
FIG. 12 is a diagram illustrating the construction of the spectroscopic analyzer and its moving mechanism of a third embodiment of optical measuring apparatus in accordance with the present invention.
Figure 13:
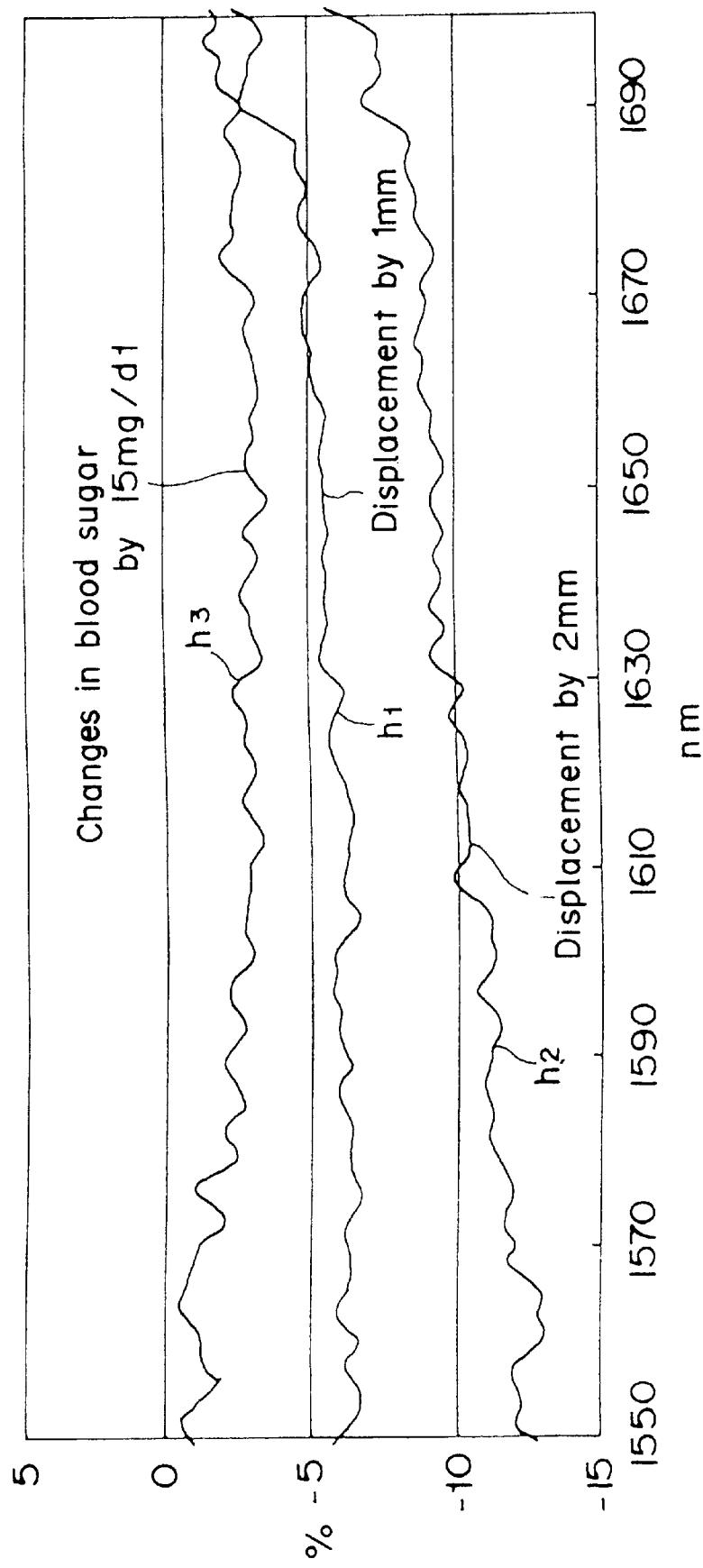
FIG. 13 is measurement data illustrating changes in measurements of blood sugar due to changes in the incidence location of light incident on a measured object.
Figure 14:
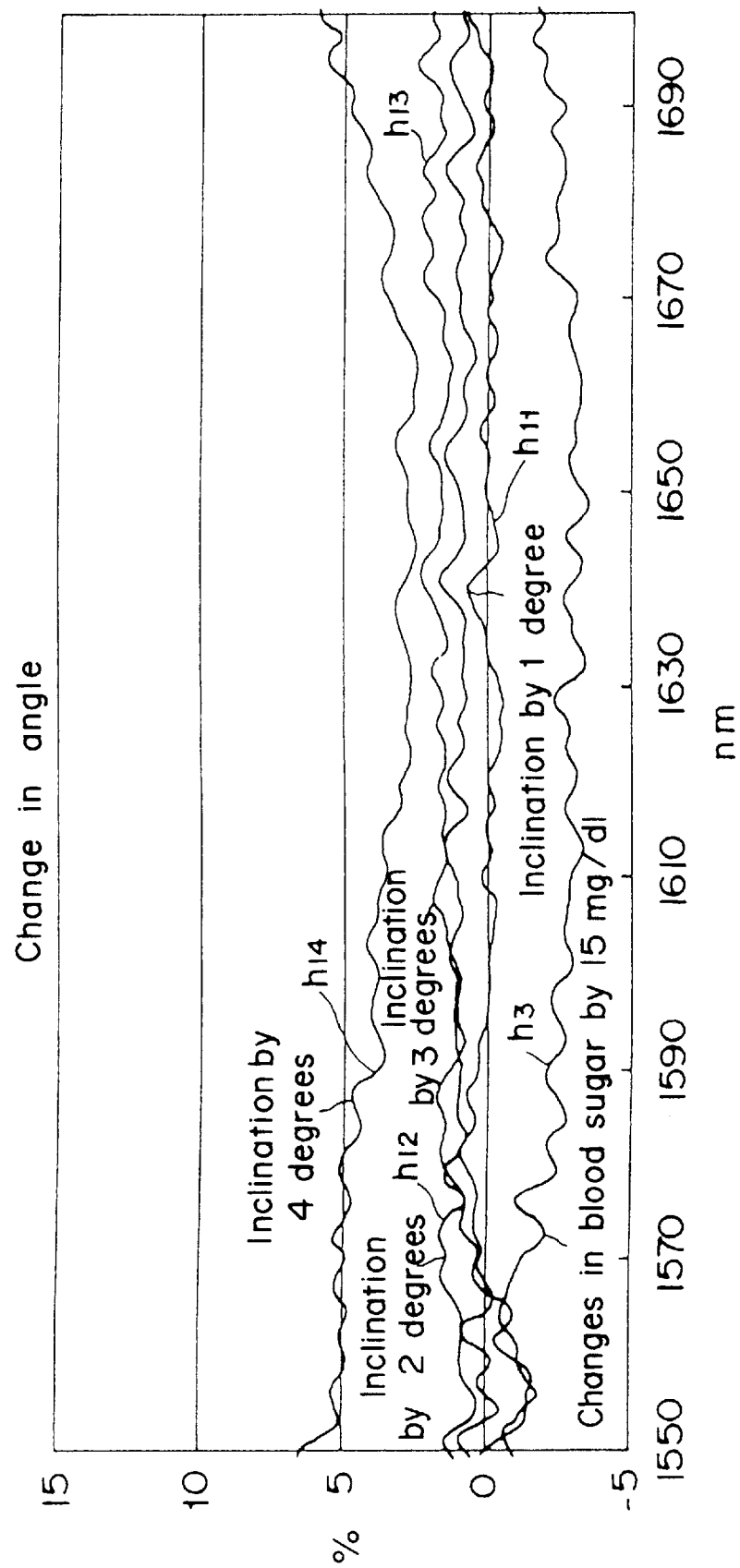
FIG. 14 is measurement data illustrating changes in measurements of blood sugar due to changes in the incidence angle of light incident on a measured object.
Figure 15:
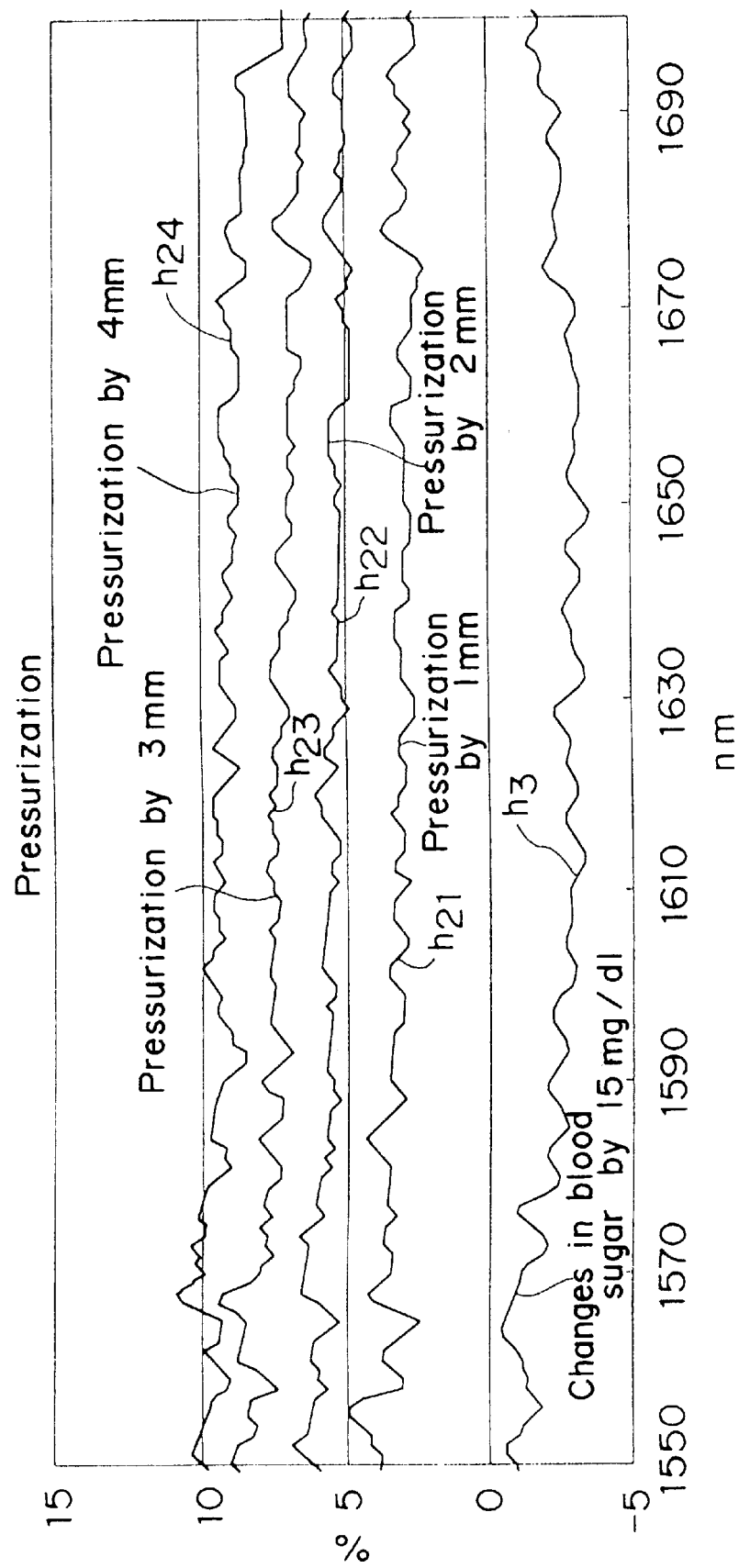
FIG. 15 is measurement data illustrating changes in measurements of blood sugar due to changes in contact pressure between a measured object and the mounting base.

FIG. 12 illustrates the optical measuring apparatus of another embodiment in accordance with the present invention. The optical measuring apparatus 1b forms an opening 105 at the location of the pressing member 28 opposite to the transmittance opening 7a of the mounting base 7, in the optical measuring apparatus of the second embodiment described with reference to FIG. 11. The optical measuring apparatus 1b directs the light transmitted by the human hand 2 into a light receiving sensor 14 through the opening 105 and an optical fiber 102. The construction of the part other than the arrangement of the optical fiber is the same as the corresponding part of the optical measuring apparatus 1a described with reference to FIG. 11. Therefore, in FIG. 12, the components corresponding to those in FIG. 11 are denoted by the same numerals, and redundant descriptions are omitted. According to this construction, the transmitted light transmitted by the human hand 2 can be detected with the optical measuring apparatus 1b of a compact shape by the use of the optical fibers 101, 102, so that the glucose concentration can be measured based on the detected transmitted light.

Possibilities of Industrial Applications

According to the present invention, when restoring the measuring location, the present invention takes a picture of the measured object to compare the pattern of that image with the pattern of the registered image and detects the part of the measured object corresponding to the marked part of the registered image. Therefore, the measuring location can be restored with a high degree of reproducibility.

The present invention further detects by pattern recognition the part corresponding to the marked part of the registered image, from the pattern of the image of the measured object taken during the restoration of the measuring location. Therefore, the measuring location can be restored with a high degree of reproducibility without depending on human eyes.

The present invention further detects with human eyes the part corresponding to the marked part of the registered image, from the pattern of the image of the measured object during the restoration of the measuring location. Therefore, the measuring location can be easily restored.

The present invention further stores information that identifies the measured object together with the marked image, so that the measured object having the mark can be easily identified.

The present invention further detects, from the pattern of the image obtained from taking a picture of an organism, a part on the organism corresponding to the marked part of the registered image having a feature to determine the measuring location. Therefore, when the concentration of a particular component within the organism is detected based on the transmitted or reflected light by projecting the measuring light onto the organism, the measuring location can be restored with a high degree of reproducibility.

According to the present invention, during the restoration of the measuring location, the optical measuring apparatus compares the pattern of the registered image with the pattern of the currently taken image of the measured object, detects the location of the part corresponding to the marked part of the registered image, in the currently taken image of the measured object, and moves the projection optical system so that the measuring light should be projected onto the detected part. Therefore, the measuring location can be restored with a high degree of reproducibility.

According to the present invention, the projection optical system or the measured object mounting means moves in the directions of the X axis and Y axis that are orthogonal to the Z axis that is oriented in the direction of the optical axis of the measuring light. Therefore, the measured object can be moved in the directions of two dimensions during each measurement so that the measuring location of the measured object can be restored at a fixed place.

According to the present invention, the projection optical system moves in the direction of the Z axis. Therefore, the positional relation in the direction of the Z axis between the projection optical system and the measured object during the registration of the registered image can be restored.

According to the present invention, the projection optical system rotates around the Z axis. Therefore, the incident spot diameter of the measuring light incident on the measured object during measurement can be corrected.

According to the present invention, the measuring apparatus detects contact pressure between the measured object and the measured object mounting means, with a contact pressure sensor and reproduces the contact pressure stored in a contact pressure memory during measurement. Therefore, changes in contact pressure between the measured object and the measured object mounting base can be reduced, so that the measuring location can be restored with a higher degree of reproducibility.

According to the present invention, the optical measuring apparatus stores in an image registration means information that identifies the measured object together with the marked image. Therefore, the measured object having the marked image can be easily identified.

According to the present invention, the optical measuring apparatus moves the projection optical system or the measured object mounting means so that the measuring light should be incident on the part selected from the pattern of the image obtained from taking a picture of an organism. Therefore, the location of a part selected from the pattern of the image obtained from taking a picture of an organism can be restored with a high degree of reproducibility.

According to the present invention, during the reproduction of the measuring location, the optical measuring apparatus compares the pattern of the registered image with the pattern of the currently taken image of the measured object, detects the location of the part corresponding to the marked part of the registered image, in the currently taken image of the measured object, and moves the projection optical system so that the measuring light should be projected onto the detected part. The optical measuring apparatus then receives the light transmitted or reflected by the measured object to detect the spectral intensity and detects the concentration of a particular component within the measured object based on the detected spectral intensity. Therefore, the reproducibility for the incidence location for the measuring light incident on the measuring part of an organism can be made great.

According to the present invention, the optical measuring apparatus projects the measuring light onto a selected part of the measured object through an optical fiber. Therefore, the degree of freedom for setting the projection optical system becomes higher owing to the flexibility of the optical fiber, and the optical measuring apparatus becomes compact.

According to the present invention, the the optical measuring apparatus receives the light transmitted or reflected by the measured object through an optical fiber. Therefore, the degree of freedom for setting the receiving optical system becomes higher owing to the flexibility of the optical fiber, and the optical measuring apparatus becomes compact.

According to the present invention, the optical measuring apparatus collects the light transmitted or reflected by the measured object with an integrating sphere. Therefore, the construction is comparatively simple, and manufacturing costs for optical measuring apparatus become low.

According to the present invention the optical measuring apparatus stores in an image registration means information that identifies the measured object together with the marked image. Therefore, the measured object having the marked image can be easily identified.

According to the present invention, the optical measuring apparatus moves the projection optical system or the measured object mounting means so that the measuring light should be incident on the part selected from the pattern of the taken image of an organism. The optical measuring apparatus then measures the concentration of a particular component within the organism. Therefore, the reproducibility for the incidence location for the measuring light incident on the measuring part of an organism can be made great, so that an optical measuring apparatus having small dispersion of measurements and great reliability can be obtained.

The invention being thus described, it will be obvious that the same may be varied in many ways. Such variations are no to be regarded as a departure from the spirit and scope of the invention, and all such modifications as would be obvious to one skilled in the art are intended to be included within the scope of the following claims.

What is claimed is:

1. A measuring apparatus that has a projection optical system, projects measuring light onto a measured object, and detects a spectral intensity of the light transmitted or reflected by the measured object to measure a concentration of a particular component within the measured object based on the spectral intensity; said measuring apparatus comprising:

measured-object mounting means for mounting the measured object, image pickup means for taking a picture of the measured object, image display means for displaying an image of the measured object, image registration means, during registration of a measuring location, for storing as a registered image an image in which a part having a visually recognized feature is marked by selecting the part from a pattern of the image of the measured object displayed on said image display means, and moving means, during the restoration of the measuring location, for comparing the pattern of said registered image with a pattern of a currently taken image of the measured object to move said projection optical system so that the measuring light is projected onto a location of a part corresponding to the marked part of the registered image, in the currently taken image of the measured object; wherein the measurement is always performed by projecting the measuring light onto an identical part of the measured object;

wherein said projection optical system moves in directions of an X axis and a Y axis that are orthogonal to a Z axis that is oriented in a direction of an optical axis of the measuring light.

2. The measuring apparatus of claim 1 wherein said image registration means stores as the registered image the marked image together with information that identifies the measured object.

3. The measuring apparatus of claim 1, wherein said projection optical system moves in the direction of the Z axis.

4. The measuring apparatus of claim 1, wherein said projection optical system rotates around the Z axis.

5. The measuring apparatus of claim 1, wherein said measuring apparatus further comprises a contact pressure sensor that detects contact pressure between the measured object and said measured object mounting means, a contact pressure memory that stores an output of said contact pressure sensor, and a pressurization device that reproduces the contact pressure stored in said contact pressure memory.

6. A measuring apparatus that has a projection optical system, projects measuring light onto a measured object, and detects a spectral intensity of the light transmitted or reflected by the measured object to measure a concentration of a particular component within the measured object based on the spectral intensity; said measuring apparatus comprising:

measured-object mounting means for mounting the measured object, image pickup means for taking a picture of the measured object, image display means for displaying an image of the measured object, image registration means, during registration of a measuring location, for storing as a registered image an image in which a part having a visually recognized feature is marked by selecting the part from a pattern of the image of the measured object displayed on said image display means, and moving means, during the restoration of the measuring location, for comparing the pattern of said registered image with a pattern of a currently taken image of the measured object to move said projection optical system so that the measuring light is projected onto a location of a part corresponding to the marked part of the registered image, in the currently taken image of the measured object; wherein the measurement is always performed by projecting the measuring light onto an identical part of the measured object;

wherein said projection optical system moves in the direction of the Z axis.

7. A measuring apparatus that has a projection optical system, projects measuring light onto a measured object, and detects a spectral intensity of the light transmitted or reflected by the measured object to measure a concentration of a particular component within the measured object based on the spectral intensity; said measuring apparatus comprising:

measured-object mounting means for mounting the measured object, image pickup means for taking a picture of the measured object, image display means for displaying an image of the measured object, image registration means, during registration of a measuring location, for storing as a registered image an image in which a part having a visually recognized feature is marked by selecting the part from a pattern of the image of the measured object displayed on said image display means, and moving means, during the restoration of the measuring location, for comparing the pattern of said registered image with a pattern of a currently taken image of the measured object to move said projection optical system so that the measuring light is projected onto a location of a part corresponding to the marked part of the registered image, in the currently taken image of the measured object; wherein the measurement is always performed by projecting the measuring light onto an identical part of the measured object;

wherein said projection optical system rotates around the Z axis.

8. A measuring apparatus that has a projection optical system, projects measuring light onto a measured object, and detects a spectral intensity of the light transmitted or reflected by the measured object to measure a concentration of a particular component within the measured object based on the spectral intensity; said measuring apparatus comprising:

measured-object mounting means for mounting the measured object, image pickup means for taking a picture of the measured object, image display means for displaying an image of the measured object, image registration means, during registration of a measuring location, for storing as a registered image an image in which a part having a visually recognized feature is marked by selecting the part from a pattern of the image of the measured object displayed on said image display means, and moving means, during the restoration of the measuring location, for comparing the pattern of said registered image with a pattern of a currently taken image of the measured object to move said protection optical system so that the measuring light is projected onto a location of a part corresponding to the marked part of the registered image, in the currently taken image of the measured object; wherein the measurement is always performed by projecting the measuring light onto an identical part of the measured object;

wherein said measuring apparatus further comprises a contact pressure sensor that detects contact pressure between the measured object and said measured object mounting means, a contact pressure memory that stores an output of said contact pressure sensor, and a pressurization device that reproduces the contact pressure stored in said contact pressure memory.

9. A measuring apparatus that has a projection optical system, projects measuring light onto a measured object, and detects a spectral intensity of light transmitted or reflected by the measured object to measure a concentration of a particular component within the measured object based on the spectral intensity; said measuring apparatus comprising:

measured-object mounting means for mounting the measured object, image pickup means for taking a picture of the measured object, image display means for displaying the image of the measured object, image registration means, during the registration of the measuring location, for storing as a registered images an image in which a part having a visually recognized feature is marked by selecting the part from a pattern of the image of the measured object displayed on said image display means, measuring location identifying means during the restoration of said measuring location, for comparing the pattern of the registered image with a pattern of the currently taken image of the measured object, identifies a location of the part corresponding to the marked part of the registered image, in the currently taken image of the measured object, moving means for moving said projection optical system so that the measuring light is projected onto the part identified by said measuring location identifying means, light receiving optical means for receiving the light transmitted or reflected by the measuring part, spectral intensity detecting means for detecting the spectral intensity of the light transmitted or reflected by the measured object and received by said light receiving optical system, arithmetic processing means for computing the concentration of a particular component within the measured object based on the spectral intensity, and output means for outputting the concentration of the particular component.

10. The measuring apparatus of claim 9, wherein said projection optical system has an optical fiber.

11. The measuring apparatus of claims 9 or 10, wherein said light receiving optical system has an optical fiber.

12. The measuring apparatus of claims 9 or 10, wherein said light receiving optical system has an integrating sphere.

13. The measuring apparatus of claim 13, wherein said image registration means stores the marked image as a registered image together with information that identifies the measured object.

14. The measuring apparatus defined in claim 9, wherein said measured object is an organism.

* * * * *